United States Patent [19]

Bacon et al.

[11] Patent Number: 6,075,125
[45] Date of Patent: *Jun. 13, 2000

[54] PRODUCTION OF ANTISERA SPECIFIC TO MAJOR HISTOCOMPATIBILITY COMPLEX MOLECULES IN CHICKENS

[75] Inventors: Larry D. Bacon, Williamston; Henry D. Hunt, Okemos, both of Mich.; Janet E. Fulton, Clive, Iowa

[73] Assignee: The United States of America as represented by the Secretary of Agriculture, Washington, D.C.

[ * ] Notice: This patent issued on a continued prosecution application filed under 37 CFR 1.53(d), and is subject to the twenty year patent term provisions of 35 U.S.C. 154(a)(2).

[21] Appl. No.: 08/890,719

[22] Filed: Jul. 9, 1997

Related U.S. Application Data

[60] Provisional application No. 60/021,685, Jul. 10, 1996.
[51] Int. Cl.[7] ........................ C07K 16/28; C12N 15/85; C12N 15/63
[52] U.S. Cl. .................................. 530/389.2; 424/198.1; 435/349; 530/389.6
[58] Field of Search ....................... 424/198.1; 435/349; 530/389.6, 389.2

[56] References Cited

PUBLICATIONS

Fulton et al. Poultry Sciences 75:10, Jul. 1996.
Goodenow et al. Nature 300:231, 1992.
Bradley et al. Immunology 57: 443, 1986.
DiSanto et al. J. Immunological Methods:141:123, 1991.
Fulton et al. Poultry Science 71:10, 1992.
Hunt et al. Immunogenetics 40: 370, 1994.
Thacker et al. J. Virology 69:6439, 1995.
Fulton et al. Eur. J. Immunol. 24: 2069, Jul. 1996.
Mathias et al. J. Immunology 144: 607, 1990.

*Primary Examiner*—Christina Y. Chan
*Assistant Examiner*—Martha Lubet
*Attorney, Agent, or Firm*—M. Howard Silverstein; Randall E. Deck; John D. Fado

[57] ABSTRACT

Host cells transfected with a recombinant DNA molecule which includes a DNA sequence inserted therein encoding a heterologous chicken BFIV MHC class I protein are disclosed. The transfected cells express the heterologous BFIV protein and may be used as an immunogen to produce chicken MHC class I (BFIV) specific antisera. The antisera so produced may then be used to determine the BF haplotype of any chicken.

12 Claims, 12 Drawing Sheets

FIG 2A

|  | 5' FLANKING SEQUENCE | | | EXON 1 (SIGNAL PEPTIDE) | | | | | | | |
|---|---|---|---|---|---|---|---|---|---|---|---|
|  | 10 | 20 |  | 30 | 40 | 50 | 60 | 70 | 80 |  |  |
|  | * | * | * | * | * | * | * | * | * | * |  |
| B-FIVCON | CTTGAGAGTG | CAGCGGTGCG | AGGCG | ATG GGG CCG TGC | GGG GCG CTG | GGC CTG GGG | CTG CTC GCC | GCC GTG TGC | GGG GCG GCC |  |  |
| B-FIV2 |  |  |  | --- --- --- --- | --- --- --- | --- --- --- | --- --- --- | --- --- --- | --- --- --- |  |  |
| B-FIV19 |  |  |  | --- --- --- --- | --- --- --- | --- --- --- | --- --- --- | --- --- --- | --- --- --- |  |  |
| B-FIV5 |  |  |  | --- --C T-- --- | --- --- --- | --- --- --- | --- --- --- | --- --- --- | --- --- --- |  |  |
| B-FIV12 |  |  |  | --- --C T-- --- | --- --- --- | --- --- --- | --- --- --- | --- --- --- | --- --- --- |  |  |
| B-FIV21 |  |  |  | --- --C T-- --- | --- --- --- | --- --- --- | --- --- --- | --- --- --- | --- --- --- |  |  |
| B-FIV13 |  |  |  | --- --- --- --- | --- --- --- | --- --- --- | --- --- --- | --- --- --- | --- --- --- |  |  |
| B-FIV15 |  |  |  | --- --- --- --- | --- --- --- | --- --- --- | --- --- --- | --- --- --- | --- --- --- |  |  |
| B-FIV19V1 |  |  |  | --- --- --- --- | --- --- --- | --- --- --- | --- --- -G- | --- --- --- | --- --- --- |  |  |
| B-FIV17 |  |  |  | --- --- --- --- | --- --- --- | --- --- --- | --- --- -G- | --- --- --- | --- --- --- |  |  |
| B-FIV18 |  |  |  | --- --- --- --- | --- --- --- | --- --- --- | --- --- --- | --- --- --- | --- --- --- |  |  |

|  | EXON 2 (ALPHA 1) | | | | | | | | | |
|---|---|---|---|---|---|---|---|---|---|---|
|  | 90 | 100 | 110 | 120 | 130 | 140 | 150 | 160 | 170 |  |
|  | * | * | * | * | * | * | * | * | * | * |
| B-FIVCON | GAG CTC CAT ACC | CTG CGG TAC ATC | CGT ACG GCG ATG | ACG GAT CCC GGC | CTG GGG CTG CCG | TGG TTC GTG GAC | GTG GGG TAC GTG GAC |  |  |  |
| B-FIV2 | --- --- --- --- | --- --- --- --- | --- --- --- --- | --- --- --- --- | --- --- --- --- | --- --- --- --- | --- --- --- --- --- | ^ |  |  |
| B-FIV19 | --- --- --- --- | --- --- --- --- | --- --- --- --- | --- --- --- --- | --- --- --- --- | --- --- --A --- | --- --- --- --- --- | ^ |  |  |
| B-FIV5 | --- --- --- --- | --- --- --- --- | --- --- --- TC- | --- --- --- --- | --- --- --- --- | --- --- --A --- | -T- --- --- --- --- | ^ |  |  |
| B-FIV12 | --- --- --- --- | --- --- --- --- | --- --- --- -AA | --- --- --- --- | --- --- --- --- | --- --- --- --- | ACT --- --- --- --- | ^ |  |  |
| B-FIV21 | --- --- --- --- | --- --- --- --- | --- --- --- --- | --- --- --- --- | --- --- --- --- | --- --- --- --- | --- --- --- --- --- | ^ |  |  |
| B-FIV13 | --- --- --- --- | --- --- --- --- | --- --- --- TC- | --- --- --- --- | --- --- --- --A | --- --- --- --- | ACT --- --- --- --- | ^ |  |  |
| B-FIV15 | --- --- --- --- | --- --- --- --- | --- --- --- TC- | --- --- --- --- | --- --- --- --A | --- --- --A --- | --- --- --- -T- --- | ^ |  |  |
| B-FIV19V1 | --- --- --- --- | --- --- --- --- | --- --- --- -A- | --- --- --- --- | --- --- --- --A | --- --- --A --- | ACT --- --- --- --- | ^ |  |  |
| B-FIV17 | --- --- --- --- | --- --- --- --- | --- --- --- --- | --- --- --- --- | --- --- --- --- | --- --- --- --- | ATT --- --- --- --- | ^ |  |  |
| B-FIV18 | --- --- --- --- | --- --- --- --- | --- --- --- TT- | --- --- --- --- | --- --- --- --- | --- --- --- --- | ACT --- --- --- --- | ^ |  |  |

FIG 2B

```
              180         190         200         210         220         230         240         250         260
               *           *           *           *           *           *           *           *           *
B-FIVCON   GGG GAA CTC TTC gTG CAC TAC AAC AGC ACC GCG CGG AGG tac GTG CCC ACC GAG TGG ATA GCG GCC AAG GCG GAC CAG CAG TAC
B-FIV2     --- --- --- --- --- --- --- --- --- --- --- --- --- --- --- --- --- --- --- --- --- --- --- --- --- --- ^^^
B-FIV19    --- --- --- --- --- --- --- --- --- --- --- --- --- --- --- --- --- --- --- --- --- --- --- --- --- --- ^^^
B-FIV5     --- --- --- AC- --- --- --- --- --- --- --- --- --- --- --- --- --- --- --G --- --- --- --- --- --- --- ^^^
B-FIV12    --- --- --- --- A-- --- --- --T --- --- --- --- GCT --- --- --- --- --- --- --- --- --- --- --- --- --- ^^^
B-FIV21    --- --- --- --- --- --- --- --- --- --- --- --- GCT --- --- --- --- --- --- --- --- --C A-- --- --- --- ^^^
B-FIV13    --- --- --- AC- --- --- --- --- --- --- --- --- GCT --- --- --- --- --- --- --- --- --C A-- --- --- --- ^^^
B-FIV15    --- --- --- AC- --- --- --- --- --- --- --- --- GCT --- --- --- --- --- --- --G --- --C A-- --- --- --- ^^^
B-FIV19V1  --- --- --- A-- --- --- --T --- --- --- --- --- GCT --- --- --- --- --- --- --G --- --C A-- --- --- --- ^^^
B-FIV17    --- --- --- --- --- --- --- --- --- --- --- --- --- --- --- --- --- --- --- --- --- --- --- --- --- --- ---
B-FIV18    --- --- --- --- --- --- --- --- --- --- --- --- --- --- --- --- --- --- --- --- --- --- --- --- --- --- ---

270         280         290         300         310         320         330         340         350
               *           *           *           *           *           *           *           *           *
B-FIVCON   TGG GAT GGA CAG ACG CAG ATC CAG GGA CAG AAT GAG CAG GGC AAT GAG CAG ATT GAC CGC GAG AAC CTG GGC ATA CTG CAG CGG TAC AAC AAC CAG ACC GGC
B-FIV2     --- --- --- --- --- --- --- --- --- --- --- --- --- --- --- --- --- --- --- --- --- --- --- --- --- --- --- --- --- --- --- --- --- ---
B-FIV19    --- --- --- --- --- --- --- --- --- --- --- C-- --G --- --- --- --- --- --- --- --- --- --- --G --- --- --G --- --- --- --- --- --- ---
B-FIV5     --- --- --- --- --- --- --- --T --- --- --- --- --G --- --- --- --- --- --- --- --- --- --- --- --- --- --- --C --- --- --- --- --- ---
B-FIV12    --- --- --- --- --- --- --- --- --- --- --- C-- --- --- --C CT- --- --- --- --- --- --- --- --- --- --- --- --C --- --- --- --- --- ---
B-FIV21    --C A-- G-- --- --- --- --- --T --- --- --- C-- --G --- --- --- --- --- --- --- --- --- --- --- --- --- --- --- --- --- --- --- --- ---
B-FIV13    --C A-T G-- --- --- --- --- C-- TC- --- --- C-- --G --- --- --- --- --- A-- --- --- -T GG- --- --A --- --G --- --- --- --- --- --- ---
B-FIV15    --C A-T G-- --- --- --- --- C-- TC- --- --- C-- --- --- --- --- --- --- A-- --- --- -T GC- --- --A --- --G --- --- --- --- --- --- ---
B-FIV19V1  --- --- --- --- --- --- --- --A --- --- --- --A CA- --- --- --- --- --- --- --- --- --- --- --- --- --- --- --- --- --- --- --- --- ---
B-FIV17    --- --- --- --- --- --- --- --- T-- --- --- --- --- --- --- --- --- --- --- --- --- --- --- --- --- --- --- --C --- --- --- --- --T ---
B-FIV18    --A --- --- --- --- --- --- --- --- --- --- --- --- --- --- --- --- --- --- AT- --- --- --- --- --- --- --- --- --- --- --- --- --- ---
```

FIG 2C

EXON 3 (ALPHA 2)

| | 360 | 370 | 380 | 390 | 400 | 410 | 420 | 430 | 440 |
|---|---|---|---|---|---|---|---|---|---|
| B-FIVCON | GGG TCT CAC ACG GTG CAG TGG ATG TAC GGC ATC CTC GAG GAC GGC ACC ATC CGG GGG TAT CAG TAT GCC TAC GAT GGG AG |
| B-FIV2 | --- --- --- --- --- --- --- --- --- --- --- --- --- --- --- --- --- --- --- --- --- --- --- --- --- --- -> |
| B-FIV19 | --- --- --- --A --- --- --- --- --- --- --- --- --- --- --- --- --- --- --- --- --- --- --- --- --- --- -> |
| B-FIV5 | --- --- --- --- --- --- --- --- --- --- --G --- --- --- --- --- --- CG- --- --- --- ATG --- --- --- -> |
| B-FIV12 | --- --- --- --- --- --- --- --- --- --- --- --- --- --- --- --- --- --- --- --- --- --- --- --- --- --- -> |
| B-FIV21 | --- --- --- --A --- --- --- --- C-- --G --- --- --- --- --- --- --- --- --- --- ACA --- --- --- -> |
| B-FIV13 | --- --- --- --- --- --- --- --- --- --- --- --T --- --- --- --- --- C-- --- --- --- ATG --- --- --- -> |
| B-FIV15 | --- --- --- --- --- CT- --- --- --- --T --- --- --- --- --- --- --- C-- --- --- --- GCA --- --- --- -> |
| B-FIV19V1 | --- --- --- --A --- --- --- --- --- --- --- --- --- --- --- --- --- AG- --- --- --- C-- --- --- --- -> |
| B-FIV17 | --- --- --- --- --- C-- --- --- --- --- --- --- --- --- --- --- --- CG- --- --- --- G-- --- --- --- -> |
| B-FIV18 | --- --- --- --- --- CT- --- --- --- --- --- --- --- --- --- --- --- AG- --- --- --- G-G --- --- --- -> |

| | 450 | 460 | 470 | 480 | 490 | 500 | 510 | 520 | 530 |
|---|---|---|---|---|---|---|---|---|---|
| B-FIVCON | A GAC TTC ATT GCC GAC TTC AAA GGC ACG ATG ACG TTC ACT GCG GCA GTT CCA GAG GCA GTT CCC ACC AAG AGG AAA TGG GAG GAA GGA GAT |
| B-FIV2 | --- --C --- --- --- --- --- --- --- --- --- --- --- --- --- --- --- --- --- --- --- --- --- --- --- --- --- --- --- --- -> |
| B-FIV19 | --- --- --- --- --- --- --- --- --- --- --- --- --- --- --- --- --- --- --- --- --- --- --- --- --- --- --- --- --- --- -> |
| B-FIV5 | --- --C --- --- --- --- --- --- --- --- --- --- --- --- --- --- --- --- --- --- --- --- --- --- --- --- --- --- --- --- -> |
| B-FIV12 | --- G-- --- --- --- --- --- --- --- --- --A --- --- --- --- --- --- --- --- --- --- --- --- --- --- --- --- --- --- --- -> |
| B-FIV21 | --- --- --- --- C-- --- --- --- --- --- --A --- --- --- --- --- --- --- --- --- --- --- --- --- --- --- --- --AG AG-> |
| B-FIV13 | --- --- --- --- --- --- --- --A --T --A --- --- --- --- --- --- --- --- --- --- --- --- --- --- --- --- --- --- --G-> |
| B-FIV15 | --- --- --- --- --- --- --- --A --- --- --- --- --- --A --- --- --- --- --- --- --- --- --- --- --- --- --- --- --AG AG-> |
| B-FIV19V1 | --- --- --- --- --- --- --- --- --- --- --- --- --- --- --- --- --- --- --- --- --- --- --- --- --- --- --- --- --- --- -> |
| B-FIV17 | --- --- --- --- C-- --- --- --A --- --- --- --- --- --- --- --- --- --- --G --- --- --- --- --- --- --- --- --- --- -> |
| B-FIV18 | --- --- --- --- --- --- --- --- --- --- --- --- --- --- --- --- --- --- --- --- --- --- --- --- --- --- --- --- --T --- -> |

```
         EXON 5 (TRANSMEMBRANE)
         900           *            920           *            940           *            960           *            980           *
            *          910           *           930            *           950           *            970           *           990
B-FIVCON GAG CCG CCA CAG CCC AAC CTG GTG CCC ATC GTG GGG GTG GCG GGT GCC ATT GTG GCC ATC GCC ATC GTG GTT GGT GTT GGA TTC ATC ATC
B-FIV2   --- --- --- --- --- --- --- --- --- --- --- --- --- --- --- --- --- --- --- --- --- --- --- --- --- --- --- --- --- ---
B-FIV19  --- --- --- --- --- --- --- --- --- --- --- --- --- --- --- --- --- --T --- --- --A --- --- --- --- --- --- --- --- ---
B-FIV5   --- --- --- --- --- --- --- --- --- --- --- --- --- --- --- --- --- --T --- --- --A --- --- --- --- --- --- --- --- ---
B-FIV12  --- --- --- --- --- --- --- --- --- --- --- --- --- --- --- --- --- --T --- --- --A --- --- --- --- --- --- --- --- ---
B-FIV21  --- --- --- --- --- --- --- --- --- --- --- --- --- --- --- --- --- --T --- --- --A --- --- --- --- --- --- --- --- ---
B-FIV13  --- --- --- --- --- --- --- --- --- --- --- --- --- --- --- --- --- --- --- --- --- --- --- --- --- --- --- --- --- ---
B-FIV15  --- --- --- --- --- --- --- --- --- --- --- --- --- --- --- --- --- --- --- --- --- --- --- --- --- --- --- --- --- ---
B-FIV19V1--- --- --- --- --- --- --- --- --- --- --- --- --- --- --- --- --- --- --- --- --- --- --- --- --- --- --- --- --- ---
B-FIV17  --- --- --- --- --- --- --- --- --- --- --- --- --- --- --- --- --- --- --- --- --- --- --- --- --- --- --- --- --G ---
B-FIV18  --- --- --- --- --- --- --- --- --- --- --- --- --- --- --- --- --- --- --- --- --- --- --- --- --- --- --- --- --- ---

EXON 7
         1000          *           1020           *           1040           *           1060           *
            *         1010           *           1030          *            1050           *           1070
B-FIVCON TAC AGA CGC CAT GCA GGG AAG AAG GGG AAG GGC TAC AAC AAC ATC GCG CCC GAC AGG GAA GGT GGA TCC AGC AGC TCG AGC ACA
B-FIV2   --- --- --- --- --- --- --- --- --- --- --- --- --- --- --- --- --- --- --- --- --- --- --- --- --- --- --- ---
B-FIV19  --- --- --- --- --- --- --- --- --- --- --- --- --- --- --- --- --- --- --A --- --- --- --- --- --- --- --- ---
B-FIV5   --- --- --- --- --- --- --- --- --- --- --- --- --- --- --- --- --- --- --- --- --- --- --- --- --- --- --- ---
B-FIV12  --- --- --- --- --- --- --- --- --- --- --- --- --- --- --- --- --- --- --- --- --- --- --- --- --- --- --- ---
B-FIV21  --- --- --- --- --- --- --- --- --- --- --- --- --- --- --- --- --- --- --- --- --- --- --- --- --- --- --- ---
B-FIV13  --- --- --- --- --- --- --- --- --- --- --- --- --- --- --- --- --- --- --- --- --- --- --- --- --- --- --- ---
B-FIV15  --- --C --- --- --- --- --- --- --- --- --- --- --- --- --- --- --- --- --- --- --- --- --- --- --- --- --- ---
B-FIV19V1--- --C --- --- --- --- --- --- --- --- --- --- --- --- --- --- --- --- --- --- --- --- --- --- --- --- --- ---
B-FIV17  --- --C --- --- --- --- --- --- --- --- --- --- --- --T --- --- --- --- --- --- --- --- --- --- --- --T --- ---
B-FIV18  --- --- --- --- --- --- --- --- --- --- --- --- --- --- --- --- --- --- --- --- --- --- --- --- --- --- --- ---
```

FIG 2G

```
            EXON 8
                  1080       1090
                 *   *      *   *
B-FIVCON    GGG AGC AAC CCC GCC ATC
B-FIV2      --- --- --- --- --- ---
B-FIV19     --- --- --- --- --- -A-
B-FIV5      --- --- --- --- --- ---
B-FIV12     --- --- --- --T --- ---
B-FIV21     --- --- --- --- --- -A-
B-FIV13     --- --- --- --- --- ---
B-FIV15     --- --- --- --- --- ---
B-FIV19V1   --- --- --- --- --- ---
B-FIV17     --- --- --- --- --- ---
B-FIV18     --- --- --- --- --- -C-

3' FLANKING SEQUENCE
                 1100       1110       1120       1130       1140       1150       1160       1170
                *   *      *   *      *   *      *   *      *   *      *   *      *   *      *   *
B-FIVCON    TGAGTGCTGT GCTTCAGCCT GCAAGGAGCC AACAGTCCAC ACCAGCATTT GGGGTCGGTG ATGGGACAG CCCCATCCTC
B-FIV2      ---------- ---------- ---------- ---------- ---------- ---A------ ---------- ---------->
B-FIV19     ---------- ---------- ---------- ---------- ---------- ---A------ ---------- ---------->
B-FIV5      ---------- ---------- -------T-- ---------- ---------- ---A------ ---------- ------A--->
B-FIV12     ---------- ---------- ---------- ---------- ---------- ---------- ---------- ---------->
B-FIV21     ---------- ---------- -------T-- ---------- ---------- ---A------ ---------- ------A--->
B-FIV13     ---------- ---------- ---------- ---------- ---------- ---------- ---------- ---------->
B-FIV15     ---------- ---------- --I--G---- ---------- ---------- ---------- ---------- ------A--->
B-FIV19V1   ---------- ---------- -------T-- ---------- ---------- ---------- ---------- ---------->
B-FIV17     ---------- ---------- ---------- ---------- ---------- ---------- ---------- ---------->
B-FIV18     ---------- ---------- ---------- ---------- ---------- ---------- ---------- ---------->

1180       1190       1200       1210       1220       1230       1240       1250       1260
                *   *      *   *      *   *      *   *      *   *      *   *      *   *      *   *      *   *
B-FIVCON    TTGACCTCTC ACATCTCATT CTGCTTCCTA TGCTGACTGT TATGCTTTGC CTGCACTGCT TCCTGTGAAA TAAAATGATG GGCCATTCTG TG
B-FIV2      ---------- ---------- ---------- ---------- ---------- ---------- ---------- ---------- ---------- --
B-FIV19     ------G--G ---------- ---------- ---------- ---------- ---------- ---------- ---------- ---------- --
B-FIV5      ---G--G-CC- ---------- ---------- ---------- ---------- ---------- ---------- ---------- ---------- --
B-FIV12     ---------- ---------- ---------- ------T--- ---------- ---------- ---------- ---------- ---------- --
B-FIV21     ---------- ---------- ---------- ---------- ---------- ---------- ---------- ---------- ---------- --
B-FIV13     ---------- ---------- ---------- ---------- ---------- ---------- ---------- ---------- ---------- --
B-FIV15     ---------- ---------- ---------- ---------- ---------- ---------- ---------- ---------- ---------- --
B-FIV19V1   ---------- ---------- ---------- ---------- ---------- ---------- ---------- ---------- ---------- --
B-FIV17     ---------- ---------- ---------- ---------- ---------- ---------- ---------- ---------- ---------- --
B-FIV18     ---------- ---------- ---------- ---------- ---------- ---------- ---------- ------C--- ---------- --
```

FIG 4

Signal Peptide

```
B-FIV21    MGSCGALGLGLLLAAVCGAAA
B-FIV19v1                       RT--
B-FIV12    --P------------------
```

α1 domain

```
           1        10        20        30        40         50        60        70        80
            *                           *       ▼    *                  *                        ▼
B-FIV21    ELHTLRYIRTAMTDPGPGLPWFVDVGYVDGELFMHYNSTA■■RRAVPRTEWIAANTDQQYWDRETQIVQGSEQINRENLDILRRRYNQT■G
B-FIV19v1  --------S---------Q--------------T------  ---------------------S---TS-R----D-DG-G--Q------ -
B-FIV12    --------Q---------Q----T---------V------  --Y---------KA------GQ---G--N---D----G--Q------ -
HLA-A2     GS-SM--FF-SVSR--R-E-R-IA-----DTQ-VRFD-D-ASQ-ME--AP--E□QEGPE---G--RK-KAHS-TH-VD-GT--GY---SEA
            *      *     *          *     * * *   * * *    *       *                              ▲
           1        10        20        30        40         50        60        70        80      90
```

α2 domain

```
           90       100       110       120       130       140       150       160       170
            *        *         *         *                          *   *        *   *   *  *
B-FIV21    GSHTVQWMSGCDILEDGT■IRGYHQAAYDGRDFVAFDKGTMTLTAAVPEAVPTKRKWEEGGYAEGLKQYLEETCVEWLRRYVEYGKAELGRR
B-FIV19v1  --------Y---------- ----R-Y-------I--------F-----------------D---------------------------
B-FIV12    --------Y------G-P ----Y-M-------T--------F----------------ESEP-RW-N-----------------------
HLA-A2     ------R-Y---VGS-WRFL-----Y----K-YI-LKEDLRSW---DMA-QT--H---AAHV--Q-RA---G---------L-N--ET-Q-T
            *        *         *         *                          *   *        *   *   * **
                   100       110       120       130       140       150       160       170       180
```

α3 domain

```
         180       190       200       210       220       230       240       250       260       270
B-FIV21    ERPEVRVWGKE■ADGILTLSCRAHGFYPRPIVVSWLKDGAVRGQDAQSGGIVPNGDGTYHTWVTIDAQPGDGDKYQCRVEHASLPQPGLYSW
B-FIV19v1  ----------- ------------------A--------------------------------------------------------------
B-FIV12    ----------- -----------------------------------H----------------------------------------------
HLA-A2     DA-KTHMTHHAVS-HEA--R-W-LS---AE-TLT-QR--EDQT--TELVETR-A----FQK-AAVVVPSGQEQR-T-H-Q-EG--K-LTLR-
                 190       200       210       220       230       240       250       260       270
```

Transmembrane and Cytoplasmic domains

```
                 280       290       300       310       320       330
B-FIV21    EPP■QPNLVPIVAGVAVAIVAIAIVVGVGFIIY■■■■RRHA■GKKGKGYNIAP■■DREGGSSSST■■■GSNPSI
B-FIV19v1  --- ----------------------------     ---- ----------- -----------    ----A-
B-FIV12    --- -------------------M--------     ---- ----------- -----------    ----A-
HLA-A2     --SS--T□I---GII-□GL-LFGA□-IT-AVVAAVMW--KSSDR--GS-SQ-ASS-SAQ--DV-LTACKD
              280       290       300       310       320       330       340
```

EXPERIMENT 1

EXPERIMENT 2

EFFECTOR TO TARGET RATIO

SEQUENCE LISTING

<160> NUMBER OF SEQ ID NOS: 39

<210> SEQ ID NO 1
<211> LENGTH: 1230
<212> TYPE: DNA
<213> ORGANISM: Gallus gallus

<400> SEQUENCE: 1

| | | | | | |
|---|---|---|---|---|---|
| cttgagagtg | cagcggtgcg | aggcgatggg | gccgtgcggg | gcgctgggcc | tggggctgct | 60 |
| gctcgccgcc | gtgtgcgggg | cggcggccga | gctccatacc | ctgcggtaca | tccgtacggc | 120 |
| gatgacggat | cccggccccg | ggctgccgtg | gtacgtggac | gtggggtacg | tggacgggga | 180 |
| actcttcgtg | cactacaaca | gcaccgcgcg | gaggtacgtg | ccccgcaccg | agtggatagc | 240 |
| ggccaaggcg | gaccagcagt | actgggatgg | acagacgcag | atcggacagg | gcaatgagca | 300 |
| gattgaccgc | gagaacctgg | gcatactgca | gcggcgctac | aaccagaccg | gcgggtctca | 360 |
| cacggtgcag | tggatgtacg | gctgtgacat | cctcgagggc | ggcccccatcc | ggggtatta | 420 |
| tcagatggcc | tacgatggga | gagacttcac | tgccttcgac | aaaggcacga | tgacgttcac | 480 |
| tgcggcagtt | ccagaggcag | ttcccaccaa | gaggaaatgg | gaggaaggag | attatgctga | 540 |
| ggggctgaag | cagtacctgg | aggaaacctg | cgtggagtgg | ctgcggagat | acgtggaata | 600 |
| cgggaaggct | gagctgggca | ggagagagcg | gcccgaggtg | cgagtgtggg | ggaaggaggc | 660 |
| cgacgggatc | ctgaccttgt | cctgccgcgc | tcacggcttc | tacccgcggc | ccatcgttgt | 720 |
| cagctggctg | aaggacggcg | cggtgcgggg | ccaggacgcc | cactcggggg | gcatcgtgcc | 780 |
| caacggcgac | ggcacctacc | acacctgggt | caccatcgat | gcgcagccgg | gggacgggga | 840 |
| caagtaccag | tgccgcgtgg | agcacgccag | cctgccccag | cccggcctct | actcgtggga | 900 |
| gccgccacac | cccaacctgg | tgcccatcgt | ggcggggtg | gccgtcgcca | ttgtggccat | 960 |
| tgccatcatg | gttggtgttg | gattcatcat | ctacagacgc | catgcaggga | agaaggggaa | 1020 |
| gggctacaac | atcgcgcccg | acagggaagg | tggatccagc | agctcgagca | cagggagcaa | 1080 |
| ccccgccatc | tgagtgctgt | gcttcagcct | gcaaggagcc | aacagtccac | accagcattt | 1140 |
| ggggtcagtg | atgggcacag | ccccatcctc | ttgacctctc | acatctcatt | ctgcttccta | 1200 |
| tgctgactgt | tatgctttgc | ctgcactgct | | | | 1230 |

<210> SEQ ID NO 2
<211> LENGTH: 1230
<212> TYPE: DNA
<213> ORGANISM: Gallus gallus

<400> SEQUENCE: 2

| | | | | | |
|---|---|---|---|---|---|
| cttgagagtg | cagcggtgcg | aggcgatggg | ctcgtgcggg | gcgctgggcc | tggggctgct | 60 |
| gctcgccgcc | gtgtgcgggg | cggcggccga | gctccatacc | ctgcggtaca | tctctacggc | 120 |
| gatgacggat | cccggccccg | ggctgccgtg | gttcgtggtc | gtggggtacg | tggacgggga | 180 |
| actcttcacg | cactacaaca | gcaccgcgcg | gaggtacgtg | ccccgcaccg | agtggatggc | 240 |
| ggccaaggcg | gacgagcagt | actgggatgg | acagacgcag | atcggacagg | gcaatgagca | 300 |
| gattgaccgc | gagaacctgg | acatactgcg | gcggcgctac | aaccagaccg | gcgggtctca | 360 |
| cacggtgcag | tggatgtacg | gctgtgacat | cctcgaggac | ggcaccatcc | ggggtatta | 420 |
| tcagacagcc | tacgatggga | gagacttcat | tgccttcgac | aaaggcacga | tgacgttcac | 480 |
| tgcggcagtt | ccagaggcag | ttcccaccaa | gaggaaatgg | gaggaaggag | attatgctga | 540 |

-continued

```
ggggctgaag cagtacctgg aggaaacctg cgtggagggg ctgcggagat acgtggaata      600
cgggaaggct gagctgggca ggagagagcg gcccgaggtg cgagtgtggg ggaaggaggc      660
cgacgggatc ctgaccttgt cctgccgcgc tcacggcttc tacccgcggc ccatcgttgt      720
cagctggctg aaggacggcg cggtgcgggg ccaggacgcc cagtcggggg gcatcgtgcc      780
caacggcgac ggcacctacc acacctgggt caccatcgat gcgcagccgg gggacgggga      840
caagtaccag tgccgcgtgg agcacgccag cctgccccag cccggcctct actcgtggga      900
gccgccacag cccaacctgg tgcccatcgt ggcggggtg gccgtcgcca ttgtggccat       960
tgccatcatg gttggtgttg gattcatcat ctacagacgc catgcaggga agaaggggaa     1020
gggctacaac atcgcgcccg acaaggaagg tggatccagc agctcgagca cagggagcaa     1080
ccccaccatc tgagtgctgt gcttcagcct gtaaggagcc aacagtccac accagcattt     1140
ggggtcggtg atggacacag ccccatcctc ttgacctctc acgtctcgtt ctgcttccta     1200
tgctgactgt tatgctttgc ctgcactgct                                       1230

<210> SEQ ID NO 3
<211> LENGTH: 1230
<212> TYPE: DNA
<213> ORGANISM: Gallus gallus

<400> SEQUENCE: 3
cttgagagtg cagcggtgcg aggcgatggg gccgtgcggg gcgctgggcc tggggctgct       60
gctcgccgcc gtgtgcgggg cggcggccga gctccatacc ctgcggtaca tccgtacggc      120
gatgacggat cccggccccg ggcagccgtg gttcgtgact gtggggtatg tggacgggga      180
actcttcgtg cactacaaca gcaccgcgcg gaggtacgtg ccccgcaccg agtggatagc      240
ggccaacacg gaccagcagt actgggatgg acagacgcag atcggacagc tcaatgagca      300
gattaaccgc gagaacctgg gcatacggca gcggcgctac aaccagactg gcgggtctca      360
cacggtgcag tggatgttcg gctgtgacat cctcgaggat ggcaccatcc ggggggtatcg     420 tcagtctgcc tacgatggga gagacttcat tgccctcgac aaagacatga agacgttcac      480
tgcggcagtt ccagaggcag ttcccaccaa gaggaaatgg gaggaagaga gtgaacctga      540
gaggtggaag aattacctgg aggaaacctg cgtggagtgg ctgcggagat acgtggaata      600
cgggaaggct gagctgggca ggagagagcg gcccgaggtg cgagtgtggg ggaaggaggc      660
cgacgggatc ctgaccttgt cctgccgcgc tcacggcttc tacccgcggc ccatcgttgt      720
cagctggctg aaggacggcg cggtgcgggg ccaggacgcc cactcggggg gcatcgtgcc      780
caacggcgac ggcacctacc acacctgggt caccatcgat gcgcagccgg gggacgggga      840
caagtaccag tgccgcgtgg agcacgccag cctgccccag cccggcctct actcgtggga      900
gccgccacag cccaacctgg tgcccatcgt ggcggggtg gccgtcgcca ttgtggccat       960
cgccatcgtg gttggtgttg gattcatcat ctacagacgc catgcaggga agaaggggaa     1020
gggctacaac attgcgcccg acagggaagg tggatccagc agctcgagca cagggagcaa     1080
ccccaccatc tgagtgctgt gcttcagcct gtaaggagcc aacagtccac accagcattt     1140
ggggtcggtg atgggcacag ccccatcctc ttgacctctc acatctcatt ctgcttccta     1200
tgctgactgt tatgctttgc ctgcactgct                                       1230

<210> SEQ ID NO 4
<211> LENGTH: 1145
<212> TYPE: DNA
```

<213> ORGANISM: Gallus gallus

<400> SEQUENCE: 4

| | | | | | |
|---|---|---|---|---|---|
| cttgagagtg | cagcggtgcg | aggcgatggg | gccgtgcggg | gcgctgggcc | tggggctgct | 60 |
| gctcgccgcc | gtgtgcgggg | cggcggccga | gctccatacc | ctgcggtaca | tccatacggc | 120 |
| gatgacggat | cccggccccg | ggctgccgtg | gttcgtgatt | gtggggtacg | tggacgggga | 180 |
| actcttcatg | cactacaaca | gcactgcgcg | gagggctgtg | ccccgcaccg | agtggatggc | 240 |
| ggccaaggcg | gaccagcagt | actgggatgg | acagacgcag | atcgaacagc | acaatgagca | 300 |
| gattgaccgc | gagaacctgg | gcacactgca | gcggcgctac | aaccagaccg | gcgggtctca | 360 |
| cacggtgcag | cggatgtccg | gctgtgacat | cctcgaggac | ggcaccatcc | ggggtatta | 420 |
| tcaggaggcc | gacgatggga | gagacttcat | tgccttcgac | aaaggcacga | tgacgttcac | 480 |
| tgcggcagtt | ccagaggcag | ttcccaccaa | gaggaaatgg | gaggaaggag | attatgctga | 540 |
| ggggctgaag | cagtacctgg | aggaaacctg | cgtggagtgg | ctgcggagat | acgtggaata | 600 |
| cgggaaggct | gagctgggca | ggagagagcg | gcccgaggtg | cgagtgtggg | ggaaggaggc | 660 |
| cgacaggatc | ctgaccttgt | cctgccgcgc | tcacggcttc | tacccgcggc | ccatcgttgt | 720 |
| cagctggctg | aaggacggcg | cggtgcggga | ccaggacgcc | cagtcggggg | gcatcgtgcc | 780 |
| caacggcgac | ggcacctacc | acacctgggt | caccatcgat | gcgcagccgg | gggacgggga | 840 |
| caagtaccag | tgccgcgtgg | agcacgccag | cctgccccag | cccggcctct | actcgtggga | 900 |
| gccgccacag | cccaacctgg | tgcccatcgt | ggcggggtg | gccgtcgcca | ttgtggccat | 960 |
| cgccatcgtg | gttggtgttg | gattcatcat | ctacagacgc | cacgcaggga | agaaggggaa | 1020 |
| gggctacaac | atcgcgcccg | acagggaagg | tggatccagc | agcttgagca | cagggagcaa | 1080 |
| ccccgccatc | tgagtgctgt | gcttcagcct | gtaaggagcc | aacagtccac | accagcattt | 1140 |
| ggggt | | | | | 1145 |

<210> SEQ ID NO 5
<211> LENGTH: 1112
<212> TYPE: DNA
<213> ORGANISM: Gallus gallus

<400> SEQUENCE: 5

| | | | | | |
|---|---|---|---|---|---|
| cttgagagtg | cagcggtgcg | aggcgatggg | gccgtgcggg | gcgctgggcc | tggggctgct | 60 |
| gctcggcgcc | gtgtgcgggg | cggcggccga | gctccatacc | ctgcggtaca | tctttacggc | 120 |
| gatgacggat | cccggccccg | ggctgccgtg | gttcgtgact | gtggggtacg | tggacgggga | 180 |
| actcttcgtg | cactacaaca | gcaccgcgcg | gagggctgtg | ccccgcaccg | agtggatggc | 240 |
| ggccaaggcg | gaccagcagt | actggaatgg | acagacgcag | atcgtacagg | gcaatgagca | 300 |
| gattatccgc | gagaacctgg | gcatactgca | gcggcgctac | aaccagaccg | gcgggtctca | 360 |
| cacggtgcag | ctgatgtacg | gctgtgacat | cctcgaggac | ggcaccatcc | ggggtatag | 420 |
| tcagtatgcc | tacgatggga | gagacttcat | tgccctcgac | aaagacacga | agacgttcac | 480 |
| tgcggcagtt | ccagaggcag | ttcccagcaa | gaggaaatgg | gaggaagtag | attatgctga | 540 |
| gagctggaag | aattacctgg | aggcaacctg | cgtggagtgg | ctgcggagat | acgtggaata | 600 |
| cgggaaggct | gagctgggca | ggagagagcg | gcccgaggtg | cgagtgtggg | ggaaggaggc | 660 |
| cgacgggatc | ctgaccttgt | cctgccgcgc | tcacggcttc | tacccgcggc | ccatcgccgt | 720 |
| cagctggctg | aaggacggca | cggtgcggga | ccaggacgcc | cactcggggg | gcatcatgcc | 780 |
| caacggcgac | ggcacctacc | acacctgggt | caccatcgat | gcgcagccgg | gggacgggga | 840 |

```
caagtaccag tgccgcgtgg agcacgccag cctgccccag cccggcctct actcgtggga      900
gccgccacag cccaacctgg tgcccatcgt ggcgggggtg gccgtcgcca ttgtggccat      960
cgccatcgtg gttggtgttg gattcatcgt ctacagacgc catgcaggga agaagggaa     1020 gggctacaac atcgcgcccg ggagcaaccc cgccacctga gtgctgtgct tcagcctgca    1080
aggagccaac agtccacacc agcatttggg gt                                   1112

<210> SEQ ID NO 6
<211> LENGTH: 1230
<212> TYPE: DNA
<213> ORGANISM: Gallus gallus

<400> SEQUENCE: 6
cttgagagtg cagcggtgcg aggcgatggg ctcgtgcggg gcgctgggcc tgggctgct       60 gctcgccgcc gtgtgcgggg cggcggccga gctccatacc ctgcggtaca tccgtacggc     120
gatgacggat cccggccccg ggctgccgtg gttcgtggac gtggggtacg tggacgggga     180
actcttcatg cactacaaca gcaccgctcg gagggctgtg ccccgcaccg agtggatagc     240
ggccaacacg gaccagcagt actgggacag agagacgcag atcgtacagg gcagtgagca     300
gattaaccgc gagaacctgg acatactgcg gcggcgctac aaccagaccg gcgggtctca     360
cacagtgcag tggatgtccg gctgtgacat cctcgaggat ggcaccatcc ggggtatca     420 tcaggcagcc tacgatggga gagacttcgt tgccttcgac aaaggcacga tgacgttaac     480
tgcggcagtt ccagaggcag ttcccaccaa gaggaaatgg gaggaaggag ttatgctga     540 ggggctgaag cagtacctgg aggaaacctg cgtggagtgg ctgcggagat atgtggaata     600
cgggaaggct gagctgggca ggagagagcg acccgaggtg cgagtgtggg ggaaggaggc     660
cgacgggatc ctgaccttgt cctgccgcgc tcacggcttc tacccgcggc ccatcgttgt     720
cagctggctg aaggacggcg cggtgcgggg ccaggacgcc cagtcggggg gcatcgtgcc     780
caacggcgac ggcacgtacc acacctgggt caccatcgat gcgcagccgg gggacgggga     840
caagtaccag tgccgcgtgg agcacgccag cctgccccag cccggcctct actcgtggga     900
gccgccacag cccaacctgg tgcccatcgt ggcgggggtg gctgtcgcca ttgtggccat     960
cgccatcgtg gttggtgttg gattcatcat ctacagacgc catgcaggga agaagggaa    1020 gggctacaac atcgcgcccg acagggaagg tggatccagc agctcgagca cagggagcaa    1080
cccctccatc tgagtgctgt gcttcagcct gcaaggagca acagtccac accagcattt    1140 ggggtcggtg atggacacag ccccatcctc ttgacctctc agatgtccct ctgcttccta    1200
tgctgactgt tattctttgc ctgcactgct                                      1230

<210> SEQ ID NO 7
<211> LENGTH: 1197
<212> TYPE: DNA
<213> ORGANISM: Gallus gallus

<400> SEQUENCE: 7
cttgagagtg cagcggtgcg aggcgatggg gccgtgcggg gcgctgggcc tgggctgct       60 gctcgccgcc gtgtgcgggg cggcggccga gctccatacc ctgcggtaca tccgtacggc     120
gatgacggat cccggccccg ggctgccgtg gtacgtggac gtggggtacg tggacgggga     180
actcttcgtg cactacaaca gcaccgcgcg gaggtacgtg ccccgcaccg agtggatagc     240
ggccaaggcg gaccagcagt actgggatgg acagacgcag atcggacagc gcagtgagca     300
```

```
gattgaccgc gagaacctgg gcatactgca gcggcgctac aaccagaccg gcgggtctca    360
cacagtgcag tggatgtacg gctgtgacat cctcgaggac ggcaccatcc ggggtatcg    420 tcagtatgcc tacgatggga gagacttcat tgccttcgac aaaggcacga tgacgttcac    480
tgcggcagtt ccagaggcag ttcccaccaa gaggaaatgg gaggaaggag attatgctga    540
ggggctgaag cagtacctgg aggaaacctg cgtggagtgg ctgcggagat acgtggaata    600
tgggaaggct gagctgggca ggagagagcg gcccgaggtg cgagtgtggg ggaaggaggc    660
cgacgggatc ctgaccttgt cctgccgcgc tcacggcttc tacccgcggc ccatcgccgt    720
cagctggctg aaggacggcg cggtgcgggg ccaggacgcc cactcggggg gcatcgtgcc    780
caacggcgac ggcacctacc acacctgggt caccatcgat gcgcagccgg gggacgggga    840
caagtaccag tgccgcgtgg agcacgccag cctgccccag cccggcctct actcgtggga    900
gccgccacag cccaacctgg tgcccatcgt ggcgggggtg gccgtcgcca ttgtggccat    960
tgccatcatg gttggtgttg gattcatcat ctacagacgc catgcaggga agaaggggaa    1020
gggctacaac atcgcgcccg ggagcaaccc cgccatctga gtgctgtgct cagcctgca    1080 aggagccaac agtccacacc agcatttggg gtcagtgatg ggcacagccc atcctcttg    1140 acctctcaca tctcattctg cttcctatgc tgactgttat gctttgcctg cactgct     1197
```

<210> SEQ ID NO 8
<211> LENGTH: 1230
<212> TYPE: DNA
<213> ORGANISM: Gallus gallus

<400> SEQUENCE: 8

```
cttgagagtg cagcggtgcg aggcgatggg ctcgtgcggg gcgctgggcc tggggctgct     60
gctcgccgcc gtgtgcgggg cggcggccga gctccatacc ctgcggtaca tccaaacggc    120
gatgacggat cccggccccg ggcagccgtg gttcgtgact gtggggtacg tggacggggga    180 actcttcgtg cactacaaca gcaccgcgcg gaggtacgtg ccccgcaccg agtggatagc    240
ggccaaggcg gaccagcagt actgggatgg acagacgcag atcggacagg caatgagca    300 gattgaccgc gagaacctgg gcatactgca gcggcgctac aaccagaccg gcgggtctca    360
cacggtgcag tggatgtacg gctgtgacat cctcgagggc ggccccatcc ggggtatta    420 tcagatggcc tacgatggga gagacttcac tgccttcgac aaaggcacga tgacgttcac    480
tgcggcagtt ccagaggcag ttcccaccaa gaggaaatgg gaggaagaga gtgaacctga    540
gaggtggaag aattacctgg aggaaacctg cgtggagtgg ctgcggagat acgtggaata    600
cgggaaggct gagctgggca ggagagagcg gcccgaggtg cgagtgtggg ggaaggaggc    660
cgacgggatc ctgaccttgt cctgccgcgc tcacggcttc tacccgcggc ccatcgttgt    720
cagctggctg aaggacggcg cggtgcgggg ccaggacgcc cactcggggg gcatcgtgcc    780
caacggcgac ggcacctacc acacctgggt caccatcgat gcgcagccgg gggacgggga    840
caagtaccag tgccgcgtgg agcacgccag cctgccccag cccggcctct actcgtggga    900
gccgccacag cccaacctgg tgcccatcgt ggcgggggtg gccgtcgcca ttgtggccat    960
tgccatcatg gttggtgttg gattcatcat ctacagacgc catgcaggga agaaggggaa    1020
gggctacaac atcgcgcccg acagggaagg tggatccagc agctcgagca cagggagcaa    1080
ccccgccatc tgagtgctgt gcttcagcct gcaaggagcc aacagtccac accagcattt    1140
ggggtcagtg atgggcacag ccccatcctc ttgacctctc acatctcatt ctgcttccta    1200
tgctgactgt tatgctttgc ctgcactgct                                    1230
```

<210> SEQ ID NO 9
<211> LENGTH: 1230
<212> TYPE: DNA
<213> ORGANISM: Gallus gallus

<400> SEQUENCE: 9

| | | | | | |
|---|---|---|---|---|---|
| cttgagagtg | cagcggtgcg | aggcgatggg | gccgtgcggg | gcgctgggcc | tggggctgct | 60 |
| gctcggcgcc | gtgtgcgggg | cggcggccga | gctccatacc | ctgcggtaca | tctctacggc | 120 |
| gatgacggat | cccggccccg | ggcagccgtg | gtacgtggac | gtggggtacg | tggacgggga | 180 |
| actcttcacg | cactacaaca | gcaccgcgcg | gagggctgtg | ccccgcaccg | agtggatagc | 240 |
| ggccaacacg | gaccagcagt | actgggacag | tgagacgcag | acctcacagc | gcactgagca | 300 |
| gattgaccgc | gatggcctgg | gcacactgca | gcggcgctac | aaccagaccg | gcgggtctca | 360 |
| cacggtgcag | ctgatgtacg | gctgtgacat | cctcgaggac | ggcaccatcc | ggggtatag | 420 |
| tcaggatgcc | tacgatggga | gagacttcat | tgccttcgac | aaagacacga | tgacgttcac | 480 |
| tgcagcagtt | ccagaggcag | ttcccaccaa | gaggaaatgg | gaggaaggag | attatgctga | 540 |
| ggggctgaag | cagtacctgg | aggaaacctg | cgtggagtgg | ctgcggagat | acgtggaata | 600 |
| tgggaaggct | gagctgggca | ggagagagcg | gcccgaggtg | cgagtgtggg | ggaaggaggc | 660 |
| cgacgggatc | ctgaccttgt | cctgccgcgc | tcacggcttc | tacccgcggc | ccatcgccgt | 720 |
| cagctggctg | aaggacggcg | cggtgcaggg | ccaggacgcc | cagtcggggg | gcattgtgcc | 780 |
| caacggcgac | ggcacctacc | acacctgggt | caccatcgat | gcgcagccgg | gggacgggga | 840 |
| caagtaccag | tgccgcgtgg | agcacgccag | cctgccccag | cccggcctct | actcgtggga | 900 |
| gccgccacag | cccaacctgg | tgcccatcgt | ggcgggggtg | gccgtcgcca | ttgtggccat | 960 |
| cgccatcgtg | gttggtgttg | gattcatcat | ctacagacgc | cctgcaggga | agaagggaa | 1020 |
| gggctacaac | atcgcgcccg | acagggaagg | tggatccagc | agctcgagca | cagggagcaa | 1080 |
| ccccgccatc | tgagtgctgt | gcttcagcct | gcaaggagcc | aacagtccac | accagcattt | 1140 |
| ggggtcggtg | atgggcacag | ccccatcctc | ttgacctctc | acatctcatt | ctgcttccta | 1200 |
| tgctgactgt | tatgctttgc | ctgcactgct | | | | 1230 |

<210> SEQ ID NO 10
<211> LENGTH: 1195
<212> TYPE: DNA
<213> ORGANISM: Gallus gallus

<400> SEQUENCE: 10

| | | | | | |
|---|---|---|---|---|---|
| cttgagagtg | cagcggtgcg | agagctccat | accctgcggt | acatctctac | ggcgatgacg | 60 |
| gatcccggcc | ccgggcagcc | gtggttcgtg | gacgtggggt | acgtggacgg | ggaactcttc | 120 |
| acgcactaca | acagcaccgc | gcggagggct | gtgccccgca | ccgagtggat | agcggccaac | 180 |
| acggaccagc | agtactggga | cagtgagacg | cagacctcac | agcgcagtga | gcagattgac | 240 |
| cgcgatgccc | tgggcatact | gcagcggcgc | tacaaccaga | ccggcgggtc | tcacacagtg | 300 |
| cagtggatgt | acggctgtga | catcctcgag | gacggcacca | tccgggggta | tcgtcagtat | 360 |
| gcctacgatg | ggagagactt | cattgccttc | gacaaaggcc | gatgacgtt | cactgcggca | 420 |
| gttccagagg | cagttcccac | caagaggaaa | tgggaggaag | gagattatgc | tgaggggctg | 480 |
| aagcagtacc | tggaggaaac | ctgcgtggag | tggctgcgga | gatacgtgga | atatgggaag | 540 |
| gctgagctgg | gcaggagaga | gcggcccgag | gtgcgagtgt | ggggaagga | ggccgacggg | 600 |

```
atcctgacct tgtcctgccg cgctcacggc ttctacccgc ggcccatcgc cgtcagctgg     660
ctgaaggacg gcgcggtgcg gggccaggac gcccagtcgg ggggcatcgt gcccaacggc     720
gacggcacct accacacctg ggtcaccatc gatgcgcagc cggggacgg ggacaagtac     780 cagtgccgcg tggagcacgc cagcctgccc cagcccggcc tctactcgtg ggagccgcca     840
cagcccaacc tggtgcccat cgtggcgggg gtggccgtcg ccattgtggc catcgccatc     900
gtggttggtg ttggattcat catctacaga cgccctgcag ggaagaaggg gaagggctac     960
aacatcgcgc cgacaggga aggtggatcc agcagctcga gcacagggag caaccccgcc    1020
atctgagtgc tgtgcttcag cctgcaaggg gccaacagtc acaccagca tttggggtcg    1080 gtgatgggca cagcccatc ctcttgacct ctcacatctc attctgcttc ctatgctgac    1140
tgttatgctt tgcctgcact gcttcctgtg aataaaatg atgggccatc ctgtg          1195
```

<210> SEQ ID NO 11
<211> LENGTH: 355
<212> TYPE: PRT
<213> ORGANISM: Gallus gallus

<400> SEQUENCE: 11

```
Met Gly Ser Cys Gly Ala Leu Gly Leu Gly Leu Leu Ala Ala Val
 1               5                   10                  15

Cys Gly Ala Ala Ala Glu Leu His Thr Leu Arg Tyr Ile Arg Thr Ala
                20                  25                  30

Met Thr Asp Pro Gly Pro Gly Leu Pro Trp Phe Val Asp Val Gly Tyr
        35                  40                  45

Val Asp Gly Glu Leu Phe Met His Tyr Asn Ser Thr Ala Arg Arg Ala
    50                  55                  60

Val Pro Arg Thr Glu Trp Ile Ala Ala Asn Thr Asp Gln Gln Tyr Trp
65                  70                  75                  80

Asp Arg Glu Thr Gln Ile Val Gln Gly Ser Gln Ile Asn Arg Glu
                85                  90                  95

Asn Leu Asp Ile Leu Arg Arg Arg Tyr Asn Gln Thr Gly Gly Ser His
            100                 105                 110

Thr Val Gln Trp Met Ser Gly Cys Asp Ile Leu Glu Asp Gly Thr Ile
        115                 120                 125

Arg Gly Tyr His Gln Ala Ala Tyr Asp Gly Arg Asp Phe Val Ala Phe
    130                 135                 140

Asp Lys Gly Thr Met Thr Leu Thr Ala Ala Val Pro Glu Ala Val Pro
145                 150                 155                 160

Thr Lys Arg Lys Trp Glu Glu Gly Gly Tyr Ala Glu Gly Leu Lys Gln
                165                 170                 175

Tyr Leu Glu Glu Thr Cys Val Glu Trp Leu Arg Arg Tyr Val Glu Tyr
            180                 185                 190

Gly Lys Ala Glu Leu Gly Arg Arg Glu Arg Pro Glu Val Arg Val Trp
        195                 200                 205

Gly Lys Glu Ala Asp Gly Ile Leu Thr Leu Ser Cys Arg Ala His Gly
    210                 215                 220

Phe Tyr Pro Arg Pro Ile Val Val Ser Trp Leu Lys Asp Gly Ala Val
225                 230                 235                 240

Arg Gly Gln Asp Ala Gln Ser Gly Gly Ile Val Pro Asn Gly Asp Gly
                245                 250                 255

Thr Tyr His Thr Trp Val Thr Ile Asp Ala Gln Pro Gly Asp Gly Asp
            260                 265                 270
```

```
Lys Tyr Gln Cys Arg Val Glu His Ala Ser Leu Pro Gln Pro Gly Leu
            275                 280                 285

Tyr Ser Trp Glu Pro Pro Gln Pro Asn Leu Val Pro Ile Val Ala Gly
        290                 295                 300

Val Ala Val Ala Ile Val Ala Ile Ala Ile Val Val Gly Val Gly Phe
305                 310                 315                 320

Ile Ile Tyr Arg Arg His Ala Gly Lys Lys Gly Lys Gly Tyr Asn Ile
                325                 330                 335

Ala Pro Asp Arg Glu Gly Gly Ser Ser Ser Ser Thr Gly Ser Asn
            340                 345                 350

Pro Ser Ile
        355

<210> SEQ ID NO 12
<211> LENGTH: 338
<212> TYPE: PRT
<213> ORGANISM: Gallus gallus

<400> SEQUENCE: 12

Arg Thr Ala Ala Glu Leu His Thr Leu Arg Tyr Ile Ser Thr Ala Met
1               5                   10                  15

Thr Asp Pro Gly Pro Gly Gln Pro Trp Phe Val Asp Val Gly Tyr Val
            20                  25                  30

Asp Gly Glu Leu Phe Thr His Tyr Asn Ser Thr Ala Arg Arg Ala Val
        35                  40                  45

Pro Arg Thr Glu Trp Ile Ala Ala Asn Thr Asp Gln Gln Tyr Trp Asp
    50                  55                  60

Ser Glu Thr Gln Thr Ser Gln Arg Ser Glu Gln Ile Asp Arg Asp Gly
65                  70                  75                  80

Leu Gly Ile Leu Gln Arg Arg Tyr Asn Gln Thr Gly Gly Ser His Thr
                85                  90                  95

Val Gln Trp Met Tyr Gly Cys Asp Ile Leu Glu Asp Gly Thr Ile Arg
            100                 105                 110

Gly Tyr Arg Gln Tyr Ala Tyr Asp Gly Arg Asp Phe Ile Ala Phe Asp
        115                 120                 125

Lys Gly Thr Met Thr Phe Thr Ala Ala Val Pro Glu Ala Val Pro Thr
130                 135                 140

Lys Arg Lys Trp Glu Glu Gly Asp Tyr Ala Glu Gly Leu Lys Gln Tyr
145                 150                 155                 160

Leu Glu Glu Thr Cys Val Glu Trp Leu Arg Arg Tyr Val Glu Tyr Gly
                165                 170                 175

Lys Ala Glu Leu Gly Arg Arg Glu Arg Pro Glu Val Arg Val Trp Gly
            180                 185                 190

Lys Glu Ala Asp Gly Ile Leu Thr Leu Ser Cys Arg Ala His Gly Phe
        195                 200                 205

Tyr Pro Arg Pro Ile Ala Val Ser Trp Leu Lys Asp Gly Ala Val Arg
    210                 215                 220

Gly Gln Asp Ala Gln Ser Gly Gly Ile Val Pro Asn Gly Asp Gly Thr
225                 230                 235                 240

Tyr His Thr Trp Val Thr Ile Asp Ala Gln Pro Gly Asp Gly Asp Lys
                245                 250                 255

Tyr Gln Cys Arg Val Glu His Ala Ser Leu Pro Gln Pro Gly Leu Tyr
            260                 265                 270

Ser Trp Glu Pro Pro Gln Pro Asn Leu Val Pro Ile Val Ala Gly Val
        275                 280                 285
```

```
Ala Val Ala Ile Val Ala Ile Ala Ile Val Val Gly Val Gly Phe Ile
        290                 295                 300

Ile Tyr Arg Arg His Ala Gly Lys Lys Gly Lys Gly Tyr Asn Ile Ala
305                 310                 315                 320

Pro Asp Arg Glu Gly Gly Ser Ser Ser Ser Thr Gly Ser Asn Pro
                325                 330                 335

Ala Ile

<210> SEQ ID NO 13
<211> LENGTH: 355
<212> TYPE: PRT
<213> ORGANISM: Gallus gallus

<400> SEQUENCE: 13

Met Gly Pro Cys Gly Ala Leu Gly Leu Gly Leu Leu Ala Ala Val
  1               5                  10                  15

Cys Gly Ala Ala Ala Glu Leu His Thr Leu Arg Tyr Ile Gln Thr Ala
                 20                  25                  30

Met Thr Asp Pro Gly Pro Gly Gln Pro Trp Phe Val Thr Val Gly Tyr
             35                  40                  45

Val Asp Gly Glu Leu Phe Val His Tyr Asn Ser Thr Ala Arg Arg Tyr
         50                  55                  60

Val Pro Arg Thr Glu Trp Ile Ala Ala Lys Ala Asp Gln Gln Tyr Trp
 65                  70                  75                  80

Asp Gly Gln Thr Gln Ile Gly Gln Gly Asn Glu Gln Ile Asp Arg Glu
                 85                  90                  95

Asn Leu Gly Ile Leu Gln Arg Arg Tyr Asn Gln Thr Gly Gly Ser His
            100                 105                 110

Thr Val Gln Trp Met Tyr Gly Cys Asp Ile Leu Glu Gly Gly Pro Ile
        115                 120                 125

Arg Gly Tyr Tyr Gln Met Ala Tyr Asp Gly Arg Asp Phe Thr Ala Phe
    130                 135                 140

Asp Lys Gly Thr Met Thr Phe Thr Ala Ala Val Pro Glu Ala Val Pro
145                 150                 155                 160

Thr Lys Arg Lys Trp Glu Glu Glu Ser Glu Pro Glu Arg Trp Lys Asn
                165                 170                 175

Tyr Leu Glu Glu Thr Cys Val Glu Trp Leu Arg Arg Tyr Val Glu Tyr
            180                 185                 190

Gly Lys Ala Glu Leu Gly Arg Arg Glu Arg Pro Glu Val Arg Val Trp
        195                 200                 205

Gly Lys Glu Ala Asp Gly Ile Leu Thr Leu Ser Cys Arg Ala His Gly
    210                 215                 220

Phe Tyr Pro Arg Pro Ile Val Ser Trp Leu Lys Asp Gly Ala Val
225                 230                 235                 240

Arg Gly Gln Asp Ala His Ser Gly Ile Val Pro Asn Gly Asp Gly
                245                 250                 255

Thr Tyr His Thr Trp Val Thr Ile Asp Ala Gln Pro Gly Asp Gly Asp
            260                 265                 270

Lys Tyr Gln Cys Arg Val Glu His Ala Ser Leu Pro Gln Pro Gly Leu
        275                 280                 285

Tyr Ser Trp Glu Pro Pro Gln Pro Asn Leu Val Pro Ile Val Ala Gly
    290                 295                 300

Val Ala Val Ala Ile Val Ala Ile Ala Ile Met Val Gly Val Gly Phe
305                 310                 315                 320
```

```
Ile Ile Tyr Arg Arg His Ala Gly Lys Lys Gly Lys Gly Tyr Asn Ile
            325                 330                 335

Ala Pro Asp Arg Glu Gly Gly Ser Ser Ser Ser Thr Gly Ser Asn
            340                 345                 350

Pro Ala Ile
        355

<210> SEQ ID NO 14
<211> LENGTH: 36
<212> TYPE: DNA
<213> ORGANISM: Gallus gallus

<400> SEQUENCE: 14
gcgggtacca agcttcttga gagtgcagcg gtgcga                              36

<210> SEQ ID NO 15
<211> LENGTH: 38
<212> TYPE: DNA
<213> ORGANISM: Gallus gallus

<400> SEQUENCE: 15
gcgtctagag cggccgctgg cccatcattt tatttcac                            38

<210> SEQ ID NO 16
<211> LENGTH: 20
<212> TYPE: DNA
<213> ORGANISM: Gallus gallus

<400> SEQUENCE: 16
caccaagagg aaatgggagg                                                20

<210> SEQ ID NO 17
<211> LENGTH: 31
<212> TYPE: DNA
<213> ORGANISM: Gallus gallus

<400> SEQUENCE: 17
tgctggtcta gactgttggc tccttgcagg c                                   31

<210> SEQ ID NO 18
<211> LENGTH: 57
<212> TYPE: DNA
<213> ORGANISM: Gallus gallus

<400> SEQUENCE: 18
cagggtatgg agctccttgt cgtcgtcgtc cttgtagtcg ccgccgccc cgcacac        57

<210> SEQ ID NO 19
<211> LENGTH: 17
<212> TYPE: DNA
<213> ORGANISM: Gallus gallus

<400> SEQUENCE: 19
ctctttacgc actacaa                                                   17

<210> SEQ ID NO 20
<211> LENGTH: 20
<212> TYPE: DNA
<213> ORGANISM: Gallus gallus

<400> SEQUENCE: 20
ctgttgtagt gcgtaaagag                                                20
```

```
<210> SEQ ID NO 21
<211> LENGTH: 24
<212> TYPE: DNA
<213> ORGANISM: Gallus gallus

<400> SEQUENCE: 21
gcgccgttgc agtattccca ggtt                                    24

<210> SEQ ID NO 22
<211> LENGTH: 27
<212> TYPE: DNA
<213> ORGANISM: Gallus gallus

<400> SEQUENCE: 22
aacctgggaa tactgcaacg gcgctac                                 27

<210> SEQ ID NO 23
<211> LENGTH: 21
<212> TYPE: DNA
<213> ORGANISM: Gallus gallus

<400> SEQUENCE: 23
gacaaaggca cgatgacgtt c                                       21

<210> SEQ ID NO 24
<211> LENGTH: 21
<212> TYPE: DNA
<213> ORGANISM: Gallus gallus

<400> SEQUENCE: 24
gacaaagaca tgaagacgtt c                                       21

<210> SEQ ID NO 25
<211> LENGTH: 21
<212> TYPE: DNA
<213> ORGANISM: Gallus gallus

<400> SEQUENCE: 25
gaacgtcatc gtgcctttgt c                                       21

<210> SEQ ID NO 26
<211> LENGTH: 21
<212> TYPE: DNA
<213> ORGANISM: Gallus gallus

<400> SEQUENCE: 26
gaacgtcttc atgtctttgt c                                       21

<210> SEQ ID NO 27
<211> LENGTH: 21
<212> TYPE: DNA
<213> ORGANISM: Gallus gallus

<400> SEQUENCE: 27
gagagtgaag ctgagaggtg g                                       21

<210> SEQ ID NO 28
<211> LENGTH: 21
<212> TYPE: DNA
<213> ORGANISM: Gallus gallus

<400> SEQUENCE: 28
```

-continued gagagtgaac ctgagaggtg g                                    21

<210> SEQ ID NO 29
<211> LENGTH: 21
<212> TYPE: DNA
<213> ORGANISM: Gallus gallus

<400> SEQUENCE: 29
ccacctctca gcttcactct c                                    21

<210> SEQ ID NO 30
<211> LENGTH: 21
<212> TYPE: DNA
<213> ORGANISM: Gallus gallus

<400> SEQUENCE: 30
ccacctctca ggttcactct c                                    21

<210> SEQ ID NO 31
<211> LENGTH: 9
<212> TYPE: PRT
<213> ORGANISM: Gallus gallus

<400> SEQUENCE: 31

Glu Ser Glu Pro Glu Arg Trp Lys Asn
 1               5

<210> SEQ ID NO 32
<211> LENGTH: 9
<212> TYPE: PRT
<213> ORGANISM: Gallus gallus

<400> SEQUENCE: 32

Gly Asp Tyr Ala Glu Gly Leu Lys Gln
 1               5

<210> SEQ ID NO 33
<211> LENGTH: 12
<212> TYPE: DNA
<213> ORGANISM: Gallus gallus

<400> SEQUENCE: 33
gctggttgta ag                                              12

<210> SEQ ID NO 34
<211> LENGTH: 12
<212> TYPE: DNA
<213> ORGANISM: Gallus gallus

<400> SEQUENCE: 34
gctggttgta ag                                              12

<210> SEQ ID NO 35
<211> LENGTH: 12
<212> TYPE: DNA
<213> ORGANISM: Gallus gallus

<400> SEQUENCE: 35
gctggttgta ag                                              12

<210> SEQ ID NO 36
<211> LENGTH: 12
<212> TYPE: DNA
<213> ORGANISM: Gallus gallus

<400> SEQUENCE: 36
gctggttgta aa                                                                12

<210> SEQ ID NO 37
<211> LENGTH: 1262
<212> TYPE: DNA
<213> ORGANISM: Gallus gallus

<400> SEQUENCE: 37
cttgagagtg cagcggtgcg aggcgatggg gccgtgcggg gcgctgggcc tggggctgct         60
gctcgccgcc gtgtgcgggg cggcggccga gctccatacc ctgcggtaca tccgtacggc        120
gatgacggat cccggccccg ggctgccgtg gttcgtggac gtggggtacg tggacgggga        180
actcttcgtg cactacaaca gcaccgcgcg gaggtacgtg ccccgcaccg agtggatagc        240
ggccaaggcg gaccagcagt actgggatgg acagacgcag atcggacagg gcaatgagca        300
gattgaccgc gagaacctgg gcatactgca gcggcgctac aaccagaccg gcgggtctca        360
cacggtgcag tggatgtacg gctgtgacat cctcgaggac ggcaccatcc ggggtgtatta       420
tcagtatgcc tacgatggga gagacttcat tgccttcgac aaaggcacga tgacgttcac        480
tgcggcagtt ccagaggcag ttcccaccaa gaggaaatgg gaggaaggag attatgctga        540
ggggctgaag cagtacctgg aggaaacctg cgtggagtgg ctgcggagat acgtggaata        600
cgggaaggct gagctgggca ggagagagcg gcccgaggtg cgagtgtggg ggaaggaggc        660
cgacgggatc ctgaccttgt cctgccgcgc tcacggcttc tacccgcggc ccatcgttgt        720
cagctggctg aaggacggcg cggtgcgggg ccaggacgcc cactcggggg gcatcgtgcc        780
caacggcgac ggcacctacc acacctgggt caccatcgat gcgcagccgg gggacgggga        840
caagtaccag tgccgcgtgg agcacgccag cctgccccag cccggcctct actcgtggga        900
gccgccacag cccaacctgg tgcccatcgt ggcggggtg gccgtcgcca ttgtggccat        960
cgccatcgtg gttggtgttg gattcatcat ctacagacgc catgcaggga agaaggggaa       1020
gggctacaac atcgcgcccg acagggaagg tggatccagc agctcgagca cagggagcaa       1080
ccccgccatc tgagtgctgt gcttcagcct gcaaggagcc aacagtccac accagcattt       1140
ggggtcggtg atgggcacag ccccatcctc ttgacctctc acatctcatt ctgcttccta       1200
tgctgactgt tatgctttgc ctgcactgct tcctgtgaaa taaatgatg gccattctg         1260
tg                                                                       1262

<210> SEQ ID NO 38
<211> LENGTH: 341
<212> TYPE: PRT
<213> ORGANISM: Homo sapiens

<400> SEQUENCE: 38

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

-continued

```
Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr Leu
            260                 265                 270

Arg Trp Glu Pro Ser Ser Gln Pro Thr Ile Pro Ile Val Gly Ile Ile
        275                 280                 285

Ala Gly Leu Val Leu Phe Gly Ala Val Ile Thr Gly Ala Val Val Ala
    290                 295                 300

Ala Val Met Trp Arg Arg Lys Ser Ser Asp Arg Lys Gly Gly Ser Tyr
305                 310                 315                 320

Ser Gln Ala Ala Ser Ser Asp Ser Ala Gln Gly Ser Asp Val Ser Leu
                325                 330                 335

Thr Ala Cys Lys Asp
            340

<210> SEQ ID NO 39
<211> LENGTH: 4
<212> TYPE: PRT
<213> ORGANISM: Gallus gallus

<400> SEQUENCE: 39

Ala Gly Cys Lys
```

PRODUCTION OF ANTISERA SPECIFIC TO MAJOR HISTOCOMPATIBILITY COMPLEX MOLECULES IN CHICKENS

CROSS-REFERENCE TO RELATED APPLICATIONS

This application hereby claims the benefit of U.S. provisional patent application Ser. No. 60/021,685, filed Jul. 10, 1996, the contents of which are incorporated by reference herein.

BACKGROUND OF THE INVENTION

1. Field of the Invention

This invention relates to the production of antibodies specific to chicken major histocompatibility complex class I molecules for the determination of chicken haplotype.

2. Description of the Prior Art

The chicken major histocompatibility complex (MHC) haplotype of chickens is intimately associated with resistance or susceptibility to viral diseases (Briles et al., 1977, Science, 195:193). Because of its strong association with disease resistance, the determination of the MHC haplotype has been of great interest to poultry breeders seeking to improve flocks (Bacon, 1987, Poultry Sci., 65:802–811).

The chicken MHC (B-complex) is comprised of three classes of highly polymorphic loci, class I (B-F), class II (B-L), and class IV (B-G). See FIG. 1. Six class I loci have been identified scattered throughout the chicken MHC (Guillemot et al., 1988, EMBO J., 7:2775) and there is evidence that more than one locus is expressed at the RNA level (Crone et al., 1985, Immunogenetics, 21:181, and Hunt and Sturgeon, 1993, Poultry Sci., vol. 72 suppl. pp 102). Recent evidence suggests that chicken class I sequences are located on two different chromosomes, or on a microchromosome containing a high frequency of recombination (Miller et al., 1994, P.N.A.S. USA, 91:4397).

The chicken MHC class I glycoproteins are biochemically and functionally similar to the mammalian class I molecules (Plachy et al., 1992, Crit. Rev. Immunol., 12:47). These 40–42 kd molecules are expressed on virtually all cells and are thought to play a central role in MHC restricted antigen presentation to cytotoxic T-cells (Maccubin and Schierman, 1986, J. Immunol., 136:12, and Weinstock et al., 1989, Eur. J. Immunol., 19:267). Recently, sequences from several alleles of the BFIV (class I) locus have been determined from both genomic libraries and cDNA (Hunt et al., 1994, Immunogenetics, 40:370–375, Kaufman et al., 1992, J. Immunol., 148:1532–1546, Kroemer et al., 1990, Immunogenetics, 31:405–409, and Pharr et al., 1994, Eur. J. Immunogenet., 21:59–66).

Traditionally the chicken MHC haplotypes have been defined using alloantisera in a hemagglutination assay. At least twenty seven different B haplotypes have been defined in chickens (Briles and Briles, 1982, Immunogenetics, 15:449–459, and Briles et al., 1982, Immunogenetics, 15:441–447). However, haplotype determination can be very complex as alloantisera show extensive cross-reactivity (Briles and Briles). The presence of immunogenic B-G (class IV) molecules, shared alleles between haplotypes, or antigenic epitopes found in more than one allele may all contribute to this cross-reactivity.

SUMMARY OF THE INVENTION

We have now discovered avian host cells transfected with a recombinant DNA molecule which includes a DNA sequence inserted therein encoding a heterologous chicken BFIV MHC class I protein. We have found that the transfected cells express the heterologous BFIV protein and may be used as an immunogen to produce chicken MHC class I (BFIV) specific antisera. The antisera so produced may then be used to determine the BF haplotype of any chicken.

It is an object of this invention to provide stable transfected cell lines which produce a heterologous chicken BFIV MHC class I protein.

It is another object of this invention to provide transfected cell lines which produce a heterologous BFIV protein having an altered epitope.

Still another object of this invention to provide a method to produce BFIV specific antisera using the transfected cell lines as immunogens.

Yet another object of this invention is to provide BFIV specific antisera which may be used to determine the B haplotype of chickens with reduced incidence of cross reactions and particularly without cross reactions resulting from antibodies to BG or other antigens.

Other objects and advantages of this invention will become readily apparent from the ensuing description.

DESCRIPTION OF THE FIGURES

FIG. 1 shows the genomic organization of the chicken MHC.

FIGS. 2A–2G show the DNA sequences of cDNA encoding various BFIV class I MHC proteins, with the sequences encoding BFIV2, BFIV5, BFIV13, BFIV17, BFIV18, BFIV21, BFIV19, BFIV12, BFIV15, BFIV19v1, and BFIV-CON represented as SEQ ID NOs. 1–10 and 37, respectively.

FIG. 3 is a diagram (not to scale) of BFIV21 cDNA showing location and direction of primers used for amplifying and mutagenizing and those restriction endonuclease sites involved in cloning.

FIG. 4 shows the predicted amino acid sequence of BFIV21 (SEQ ID no. 11). Shown aligned are the amino acid sequence of BFIV12 (SEQ ID no. 13) (Guillemot et al., 1988, ibid) and BFIV19v1 (SEQ ID no. 12) (Kaufman et al., 1992, ibid). Standard one letter amino acid codes are used with dashes indicating identity. The BFIV12 and BFIV19v1 sequences are corrected at the signal peptide-alpha 1 domain junction as described by Hunt et al. (1994, ibid). The region of the cytoplasmic domain coded by exon 7 for BFIV12 was obtained from the BFIV12 genomic sequence (Kroemer et al., 1990, ibid). Also aligned is the HLA-A2 amino acid sequence (SEQ ID NO. 38, from Walker et al., 1985, P.N.A.S. USA, 82:539) with its corresponding enumeration. Insertion of gaps for optimal alignment are shown as ■ in BF and □ in HLA sequence. Carbohydrate attachment sites are indicated by CHO.

FIG. 5 shows the $^{51}$Chromium release assay showing cytotoxicity of ALV induced T cells against RP9 target cells expressing ALV and either BFIV21, BFIV21-FLAG or BFIV13-FLAG class I sequences.

FIG. 6 shows the $^{51}$Chromium release assay showing cytotoxicity of ALV induced T cells against RP9 target cells expressing ALV and either BFIV21, BFIV13, BFIV21M34T or BFIV21D78G,R81Q class I sequences.

DEFINITIONS

The following terms are employed herein:

Cloning.

The selection and propagation of (a) genetic material from a single individual, (b) a vector containing one gene or gene fragment, or (c) a single organism containing one such gene or gene fragment.

Cloning Vector.

A plasmid, virus, retrovirus, bacteriophage or nucleic acid sequence which is able to replicate in a host cell, characterized by one or a small number of restriction endonuclease recognition sites at which the sequence may be cut in a predetermined fashion, and which contains a marker suitable for use in the identification of transfected cells, e.g., tetracycline resistance or ampicillin resistance. A cloning vector may or may not possess the features necessary for it to operate as an expression vector.

Codon.

A DNA sequence of three nucleotides (a triplet) which codes (through mRNA) for an amino acid, a translational start signal, or a translational termination signal. For example, the nucleotide triplets TTA, TTG, CTT, CTC, CTA, and CTG encode for the amino acid leucine, while TAG, TAA, and TGA are translational stop signals, and ATG is a translational start signal.

DNA Coding Sequence.

A DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxy) terminus. A coding sequence can include, but is not limited to, procaryotic sequences and cDNA from eucaryotic mRNA. A polyadenylation signal and transcription termination sequence will usually be located 3' to the coding sequence.

DNA Sequence.

A linear series of nucleotides connected to one another by phosphodiester bonds between the 3' and 5' carbons of adjacent pentoses.

Expression.

The process undergone by a structural gene to produce a polypeptide. Expression requires both transcription of DNA to RNA and translation of RNA to protein.

Expression Vector.

A replicon such as a plasmid, virus, retrovirus, bacteriophage, or nucleic acid sequence which is able to replicate in a host cell, characterized by a restriction endonuclease recognition site at which the sequence may be cut in a predetermined fashion for the insertion of a heterologous DNA sequence. An expression vector has a promoter positioned upstream of the site at which the sequence is cut for the insertion of the heterologous DNA sequence, the recognition site being selected so that the promoter will be operatively associated with the heterologous DNA sequence. A heterologous DNA sequence is "operatively associated" with the promoter in a cell when RNA polymerase which binds the promoter sequence transcribes the coding sequence into mRNA which is then in turn translated into the protein encoded by the coding sequence.

Fusion Protein.

A protein produced when two heterologous genes or fragments thereof coding for two different proteins not found fused together in nature are fused together in an expression vector. For the fusion protein to correspond to the separate proteins, the separate DNA sequences must be fused together in correct translational reading frame.

Gene.

A segment of DNA which encodes a specific protein or polypeptide, or RNA.

Genome.

The entire DNA of an organism. It includes, among other things, the structural genes encoding for the polypeptides of the substance, as well as operator, promotor and ribosome binding and interaction sequences.

Heterologous DNA.

A DNA sequence inserted within or connected to another DNA sequence which codes for polypeptides not coded for in nature by the DNA sequence to which it is joined. Allelic variations or naturally occurring mutational events do not give rise to a heterologous DNA sequence as defined herein.

Hybridization.

The pairing together or annealing of single stranded regions of nucleic acids to form double-stranded molecules.

Nucleotide.

A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. The base characterizes the nucleotide. The four DNA bases are adenine ("A"), guanine ("G"), cytosine ("C"), and thymine ("T"). The four RNA bases are A, G, C, and uracil ("U").

Phage or Bacteriophage.

Bacterial virus many of which include DNA sequences encapsidated in a protein envelope or coat ("capsid"). In a unicellular organism, a phage may be introduced by a process called transfection.

Plasmid.

A non-chromosomal, double-stranded DNA sequence comprising an intact "replicon" such that the plasmid is replicated in a host cell. When the plasmid is placed within a unicellular organism, the characteristics of that organism may be changed or transfected or transformed as a result of the DNA of the plasmid. A cell transfected by a plasmid is called a "transfectant."

Polypeptide.

A linear series of amino acids connected one to the other by peptide bonds between the alpha-amino and carboxy groups of adjacent amino acids.

Promoter.

A DNA sequence within a larger DNA sequence defining a site to which RNA polymerase may bind and initiate transcription.

Reading Frame.

The grouping of codons during translation of mRNA into amino acid sequences. During translation, the proper reading frame must be maintained. For example, the DNA sequence GCTGGTTGTAAG (SEQ ID NO:33) may be translated via mRNA into three reading frames, each of which affords a different amino acid sequence:

GCT GGT TGT AAG (SEQ ID NO. 34) - Ala-Gly-Cys-Lys (SEQ ID NO. 39)

G CTG GTT GTA AG (SEQ ID NO. 35) - Leu-Val-Val

GC TGG TTG TAA A (SEQ ID NO. 36) - Trp-Leu-(STOP)

Recombinant DNA Molecule.

A hybrid DNA sequence comprising at least two DNA sequences, the first sequence not normally being found together in nature with the second.

Ribosomal Binding Site.

A nucleotide sequence of mRNA, coded for by a DNA sequence, to which ribosomes bind so that translation may be initiated. A ribosomal binding site is required for efficient translation to occur. The DNA sequence coding for a ribosomal binding site is positioned on a larger DNA sequence downstream of a promoter and upstream from a translational start sequence.

Replicon.

Any genetic element (e.g., plasmid, chromosome, virus) that functions as an autonomous unit of DNA replication in vivo, i.e., capable of replication under its own control.

Start Codon.

Also called the initiation codon, is the first mRNA triplet to be translated during protein or peptide synthesis and immediately precedes the structural gene being translated. The start codon is usually AUG, but may sometimes also be GUG.

Structural Gene.

A DNA sequence which encodes through its template or messenger RNA (mRNA) a sequence of amino acids characteristic of a specific polypeptide.

Transfect or transform.

To change in a heritable manner the characteristics of a host cell in response to DNA foreign to that cell. A eucaryotic cell has been transfected (or a procaryotic cell transformed) by exogenous DNA when such exogenous DNA has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eucaryotic cells, a stably transfected cell is one in which the exogenous DNA has become integrated into a chromosome so that it is inherited by daughter cells through chromosome replication. This stability is demonstrated by the ability of the eucaryotic cell to establish cell lines or clones comprised of a population of daughter cells containing the exogenous DNA.

Transcription.

The process of producing mRNA from a structural gene.

Translation.

The process of producing a polypeptide from mRNA.

DETAILED DESCRIPTION OF THE INVENTION

Figure 1:
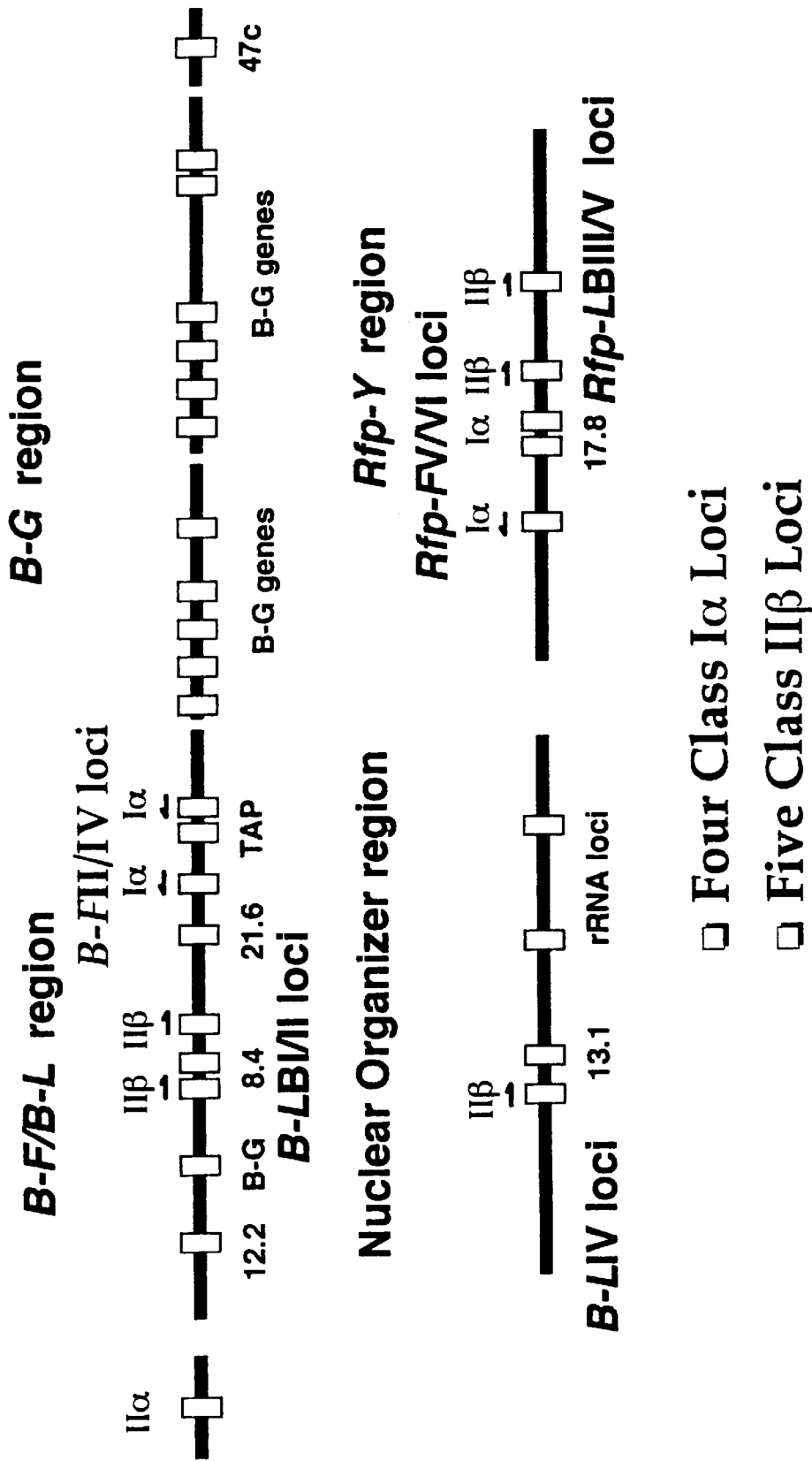

In accordance with this invention, we have created stable transfected cells which express a heterologous or foreign MHC protein. The term heterologous protein is defined herein as a class I MHC protein which is different from the native or wild type protein normally associated with the host cell to be transfected. This heterologous protein may be a class I MHC protein of a different BFIV allele than the host cell, or a class I MHC protein having an altered epitope or immunogenic region. This immunogenic region may be altered by site-directed mutation, substituting one or more different nucleotides within the heterologous MHC encoding region resulting in a change in the subsequent amino acids within the epitope of the protein, or it may be changed by alteration of nucleotides encoding the amino acids corresponding to at least a portion of an epitope from a class I MHC protein of a different BFIV allele.

In brief, the cells of this invention are produced by transfection of an appropriate host cell with recombinant DNA having a DNA sequence which encodes the above-mentioned heterologous MHC class I protein. The isolated DNA sequence encoding the heterologous MHC protein is first inserted into a recombinant DNA molecule such as a cloning vector or expression vector. These recombinant vectors are then inserted into the host cells to form stable transfectants containing the DNA that encodes the heterologous MHC protein. Transfectants producing the protein may then be identified by screening, and subsequently used to immunize a host animal for the production of antisera.

Host Cells

To minimize the production of cross-reacting antibodies, the host cells should be substantially histocompatible with the host animal to be used for production of antisera, sharing the same B haplotype and substantially the same minor histocompatibility antigens. Thus, when the host animal is immunized with the transfected cells, antibodies will only be elicited against non-self epitopes of the expressed heterologous MHC protein. In the preferred embodiment, immortal or tumor cell lines derived from inbred or congenic chicken lines or from hybrids of inbred chicken lines of known haplotype, are used as the host cells. Tumor cell lines from hybrids are particularly preferred as the hybrid birds generally exhibit greater vigor and fecundity than inbred lines. A number of tumor cell lines derived from inbred chicken lines, or their hybrids, which are suitable for use herein have been described by Nazerian (1987, Avian Pathology, 16:527–544), the contents of which are incorporated by reference herein.

Tumor cell lines for use herein may also be readily prepared using conventional in vitro viral transformation techniques. A variety of host cell types may be virally transformed to produce an immortal cell line, and the particular cell type selected is not critical. Without being limited thereto, preferred cell types include bone marrow cells, peripheral blood lymphocytes, bursal cells, spleen cells, and chicken embryo cells such as chicken embryo lymphocytes and chicken embryo fibroblasts (CEF). A variety of conventional viral transforming agents are also suitable for use herein. Preferred transforming agents include, but are not limited to, herpes simplex virus, avian erythroblastosis virus, avian myelocytomatosis virus, avian myeloblastosis virus, reticuloendotheliosis virus (REV), particularly REV strain T (REV-T), and avian leukosis virus, particularly Rous-associated virus. Generally, isolated chicken cells are suspended in a conventional tissue culture medium to which the viral transforming agent has been added in an amount effective to transform the cells. The culture media and conditions per se which are used in the transformation are not critical, and a variety of conventional culture media and culture conditions are suitable for use herein. Transformation of the virus treated cells is indicated by significant cell growth in comparison with untreated cells.

In the alternative, the tumor cell lines may be derived from tumors or lymphomas isolated from chickens. These tumors may be naturally occurring, or they may be induced in vivo as is known in the art by inoculation of the subject chicken with an effective amount of any of the above-mentioned viral transforming agents.

In an alternative embodiment, adult chicken skin fibroblasts may be used as the host cells. Not only does this process obviate the need for an established cell line, even more importantly, it does not require use of an inbred or congenic line of chickens to produce the antisera. In accordance with this embodiment, skin fibroblasts may be recovered and isolated from any normal, healthy adult chicken, and subsequently transfected with the above-mentioned recombinant vector using the same techniques described hereinbelow. Transfectants expressing the heterologous MHC protein may then be used to immunize the same bird from which the fibroblasts were initially isolated. Because the same bird is used, antibodies will only be produced against non-self epitopes of the heterologous MHC protein expressed on the surface of the fibroblasts.

DNA Sequences

Figure 2D:
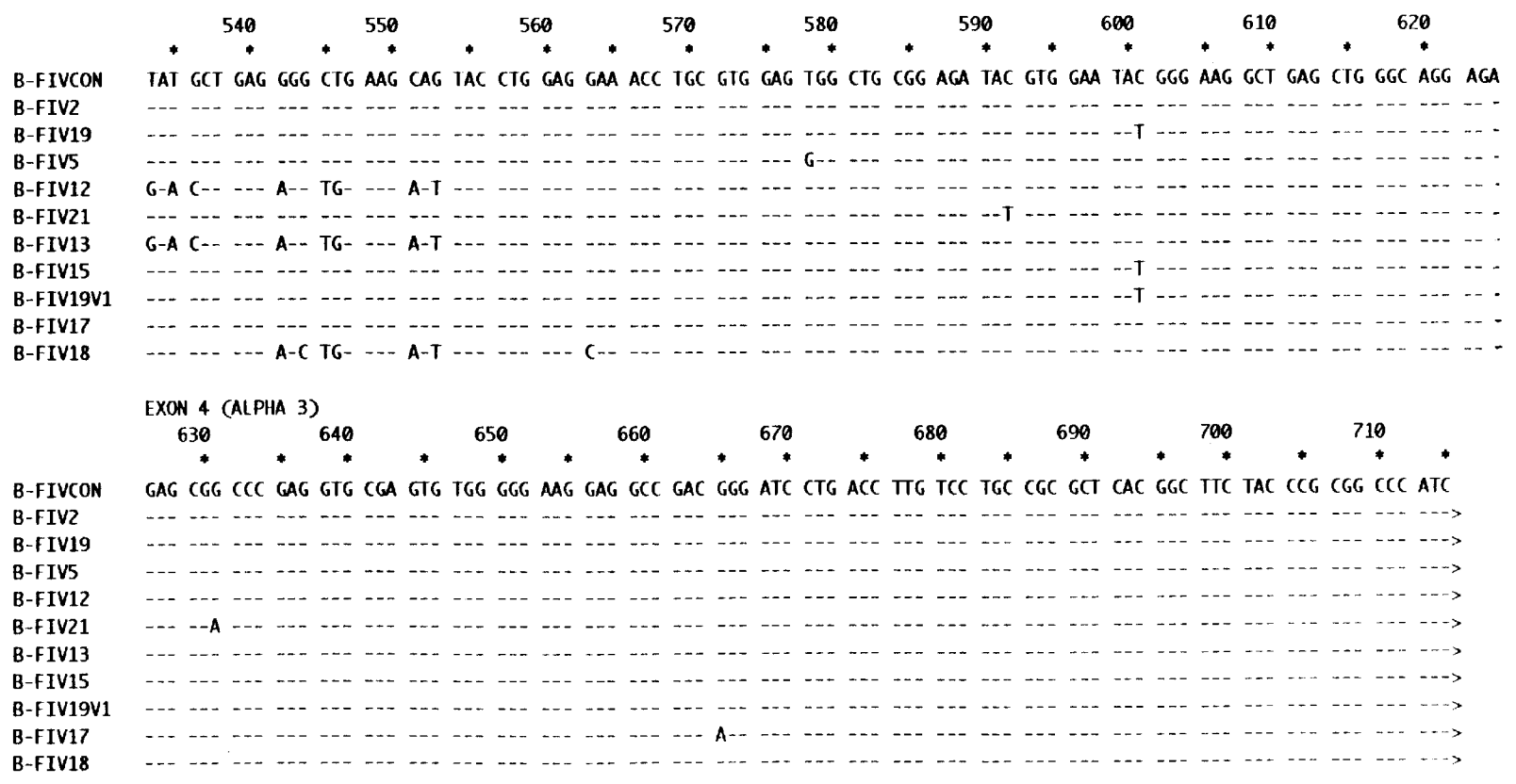
Figure 2E:
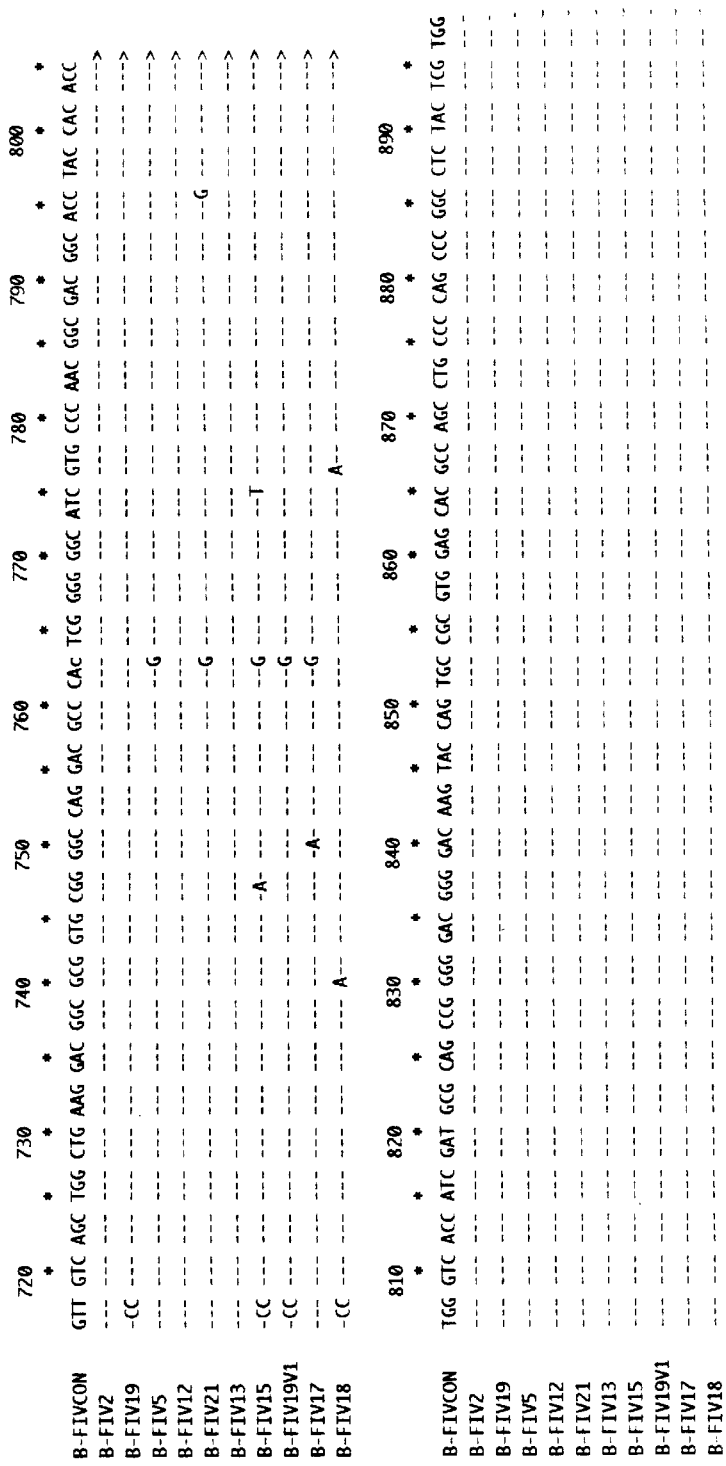

The present invention provides isolated DNA sequences which encode antigenic class I MHC proteins, particularly BFIV class I MHC proteins, effective for eliciting antibody production. Specifically, the invention encompasses both cDNA clones and genomic DNA molecules having nucleotide sequences encoding the BFIV MHC class I proteins. DNA sequences of cDNA isolated from the BFIV locus of a number of different haplotypes suitable for use herein have been described, for example, by Hunt et al. (1994, Immunogenetics, 40:370–375) and Fulton et al. (1995, Eur. J. Immunol., 25:2069–2076), the contents of each of which are incorporated by reference herein. The nucleotide sequences for cDNA encoding a number of different BFIV haplotypes which may be used herein are also shown in FIG. 2 (the sequences encoding BFIV2, BFIV5, BFIV13, BFIV17, BFIV18, BFIV21, BFIV19, BFIV12, BFIV15, and BFIV19v1, are represented as SEQ ID nos. 1–10, respectively). As shown therein, BFIVCON refers to the consensus nucleotides of the BFIV cDNA, with dashes showing identity, and polymorphisms being shown for each haplotype. The sequences are shown in their correct reading frame, with exon 1 encoding the signal peptide beginning at nucleotide number 26, and exons 5–8 encoding the cytoplasmic and transmembrane regions of the proteins. The predicted amino acid sequences for BFIV21, BFIV19v1 and BFIV12 have been compared by Fulton et al. (1995, ibid). The practitioner skilled in the art will recognize that the corresponding predicted amino acid sequences for other BFIV proteins may be readily determined from the disclosed DNA sequences.

Cloning and sequencing of BFIV cDNA for any other haplotypes may be readily performed using the techniques described by Hunt et al. (1994, ibid) and Fulton et al. (1995, ibid). BFIV sequences are most readily cloned from B-homozygous inbred or congenic chicken lines, but they may be cloned from any chicken. In general, cDNA expressed by the BFIV allele may be amplified by polymerase chain reaction (PCR), such as described by U.S. Pat. No. 4,683,195, using oligonucleotide primers specific for the untranslated flanking regions of the BFIV locus. While a variety of primers may be used, without being limited thereto, the preferred primers are 5'CTTGAGAGTG-CAGCGGTGCGA (designated BFIV.5 SEQ ID no. 14) and 5'TGGCCCATCATTTTATTTCAC (designated BFIV.3 SEQ ID no. 15). The amplification product may then be cloned into an appropriate eucaryotic vector as described hereinbelow.

Because of the degeneracy of the genetic code, there exists a finite set of nucleotide sequences which can code for a given amino acid sequence. It is understood that all such equivalent sequences encoding the BFIV class I MHC proteins are operable variants of the disclosed sequences, since all give rise to the same proteins (i.e., the same amino acid sequences) during in vivo transcription and translation, and are hence encompassed by the instant invention.

In a first embodiment, the isolated DNA sequences encoding a BFIV class I MHC protein of a haplotype of interest may be directly inserted into a vector (without further modification or alteration of epitopes) and used for cell transfection as described herein. Again, the host cell subjected to transfection and the animal subsequently immunized with the transfected cell should be of the same haplotype, but different from that of the heterologous protein. Antisera so produced will contain antibodies to epitopes present on the heterologous BFIV protein. Any epitopes resulting from amino acid polymorphisms (amino acid sequences different from other haplotypes) will elicit antibodies which are specific for that haplotype. However, any epitopes which are shared by BFIV proteins of other alleles (common polymorphisms) will of course elicit cross reactive antibodies specific for these same haplotypes.

In an alternative embodiment, we have discovered that one or more epitopes of the BFIV class I MHC proteins may be altered to produce BFIV allele specific antisera. In order to practice this embodiment, the epitopes or antigenic sites of the BFIV proteins must first be identified. Immunogenic sites on the BFIV molecules may be determined by 3-dimensional analysis of the structure or conformation of the BFIV proteins. Any amino acid residues having side chains directed outward from the molecule (exposed) may be immunogenic.

We have found that the 3-dimensional structures of the chicken BFIV class I MHC proteins may be accurately and consistently modeled after the human MHC, particularly HLA-A2, the crystal structure of which was determined by Bjorkman et al. (1987, Nature, 329:506), the contents of which are incorporated by reference herein. Modeling of BFIV proteins may be performed by the GLAXO Institute for Molecular Biology SA (Geneva, Switzerland) using the Swiss-Model Automated Protein Modeling Service, or using similar protein modeling services such as that available through the National Institutes of Health (Washington, D.C.). Alternatively, because the chicken BFIV protein may be modeled after the human HLA-A2, the predicted amino acid sequence of the BFIV protein may be aligned with that of HLA-A2 using conventional software. Immunogenic sites on the BFIV should correspond with the immunogenic sites (having outwardly directed amino acid residues) on the HLA-A2 protein.

In addition to identifying the epitopes of the BFIV MHC protein, the DNA or amino acid sequences are also examined to identify any polymorphic regions within the protein of a first haplotype wherein the predicted amino acid sequence is different from that of some or all other haplotypes.

When an epitope has been identified which possesses polymorphisms rendering it different from the corresponding epitope of most or all other BFIV alleles, the nucleotide sequence encoding that epitope may be inserted into the DNA sequence encoding a BFIV protein of a second, different allele (which does not exhibit the same polymorphism). This insertion should be at a corresponding site and may be made using conventional techniques such as splicing by overlapping extension as described in the Examples, as well as U.S. Pat. No. 5,023,171 and by Ho et al. (1989, Gene, 77:51), the contents of each of which are incorporated by reference herein. In review, a pair of mutagenizing oligonucleotide primers are prepared which are specific for and overlap the area of the DNA sequence to be altered, but which contain the desired altered or mutant nucleotide sequence (e.g., encoding the epitope of the first haplotype). PCR amplification may then be used with one of the mutagenizing primers in conjunction with a flanking primer (i.e., BFIV.5 or BFIV.3) in separate reactions with the DNA sequence encoding the BFIV protein of the second haplotype. The resulting product of each reaction may be isolated, such as by gel electrophoresis, from the template, and combined for a second PCR amplification. The second PCR amplification utilizes the same flanking primers with the annealed product as template. The product will have the same sequence as the DNA encoding the BFIV protein of the second haplotype except for the change(s) at the desired epitope. Other techniques for introducing the alteration are described, for example, by Godowski et al. (U.S. Pat. No. 5,328,837), the contents of which are incorporated by reference herein.

This DNA encoding the modified BFIV protein may then be inserted into a vector and used to transfect cells of the same second BFIV allele. Thus the cell will express a heterologous BFIV protein, different from its wild type BFIV protein only at the site of the altered epitope. When an animal having the second BFIV allele is immunized with the transfected cell, antibodies will only be produced against the altered epitope, and the antisera will be specific for BFIV proteins of the first BFIV allele.

In the alternative to inserting a foreign epitope into a BFIV protein as described above, epitopes which are cross reactive may be altered to render a shared epitope non-reactive. In this embodiment, the DNA encoding the BFIV protein of interest is altered at the codons encoding these cross reactive epitopes, rendering the resulting epitope of the modified BFIV protein non-immunogenic in the immunized host animal. For example, antiserum specific for normal BFIV protein of the B21 haplotype strongly cross reacts with BFIV protein of the B5 haplotype. The cross reactivity with B5 is due to a shared polymorphic epitope at amino acids 78 and 81 on the B21 BFIV protein. Amino acids 78 and 81 of the B21 protein may be altered by site directed mutation using the same procedure for splicing by overlapping extension described above. B21 specific antisera lacking cross-reactivity with B5 may then be produced by immunization of birds of a different haplotype with transfected cells encoding the mutant BFIV protein.

Transfection

The DNA sequences encoding the heterologous MHC protein can be used to prepare recombinant DNA molecules by cloning in any suitable vector. A variety of conventional eucaryotic cloning or expression vectors, which may be plasmids or viruses, may be employed in practicing the invention, and selection of the appropriate vector is a matter of choice. A number of eucaryotic expression vectors have been described in U.S. Pat. Nos. 4,546,082, 4,510,245, 4,446,235, and 4,443,540, the contents of each of which are incorporated by reference herein. Further, the vectors may be non-fusion vectors (i.e., those producing the antigenic MHC protein of this invention not fused to any other heterologous polypeptide), or fusion vectors (i.e., those producing the antigenic MHC protein fused to a vector encoded polypeptide). The fusion proteins will of course vary with the particular vector chosen.

Within each specific vector various sites may be selected for insertion of the isolated DNA sequence encoding the heterologous MHC protein. These sites are usually designated by the restriction enzyme or endonuclease that cuts them. The particular site chosen for insertion of the DNA sequence is determined by a variety of factors. These include size and structure of the subsequent polypeptide to be expressed, susceptibility of that polypeptide to enzymatic degradation by the host cell components, expression characteristics such as the location of start and stop codons, and other factors recognized by those skilled in the art. None of these factors alone absolutely controls the choice of insertion site. Rather, the site chosen reflects a balance of these factors, and not all sites may be equally effective for a given nucleotide sequence.

The DNA sequences may be inserted into the desired vector by known techniques. If, however, the vector is to serve as an expression vector, the vector should have a promoter, and the DNA sequence should be inserted in the vector downstream of the promoter and operatively associated therewith. While control sequences may be ligated to the coding sequence prior to insertion into the vector, preferably, the vector should be selected so as to have a promoter operable in the host cell into which the vector is to be inserted (that is, the promoter should be recognized by the RNA polymerase of the host cell). In addition, the vector should have a region which codes for a ribosome binding site positioned between the promoter and the site at which the DNA sequence is inserted so as to be operatively associated with the DNA sequence once inserted (in correct translational reading frame therewith). The vector should also be selected to provide a region which codes for a ribosomal binding site recognized by the ribosomes of the host cell into which it is to be inserted.

The antigenic heterologous MHC proteins of this invention are produced by growing the host cells transfected by the vectors described above under conditions whereby the antigen is produced. The antigens are then expressed on the surface of the host cells. The selection of the appropriate tissue culture media and growth conditions are well within the skill in the art and may be the same as those used for the viral transformation of cell lines described hereinabove.

Screening

Following transfection, samples of the cells are screened for expression of the heterologous MHC protein. In one embodiment, transfectants may be identified by screening with oligonucleotide probes complimentary to a nucleotide sequence encoding a portion of heterologous protein by Southern hybridization analysis. However, this assay only provides an indication that the recombinant DNA has been successfully incorporated into the host cell; it cannot determine if the subsequent MHC protein is expressed in correct structure or conformation. In another embodiment, the cells may be screened by immunoassay techniques using monoclonal antibodies or conventional chicken MHC antisera. The antibodies or antisera should of course be directed to products of the BFIV allele corresponding to the heterologous chicken MHC (BFIV) protein, or to that BFIV allele corresponding to the altered epitope. However, to minimize cross reactions and ensure that positive reactions are the result of reactions with the heterologous MHC protein and not other MHC antigens such as BG proteins, the assay is preferably conducted with antisera to BF MHC proteins. Without being limited thereto, techniques for the identification of suitable antisera against BF antigens and immunoassay techniques for detecting BF MHC proteins are described by Fulton et al. (1996, Immunogenetics, 43:277–288), the contents of which are incorporated by reference herein.

In the preferred embodiment, the recombinant DNA encoding the heterologous MHC protein further includes a DNA sequence encoding a detectable fusion polypeptide or tag. In this embodiment, the transfected cells are screened with both conventional antisera or antibodies to BF proteins as mentioned, as well as antibodies against the detectable tag. The tag may also be detected using conventional immunoassay techniques, and its detection provides a positive indication of expression of the recombinant protein.

Although the tag is not critical and many polypeptides may be used, it is understood that the tag should not alter the three dimensional structure of the MHC protein, particularly in the vicinity of the epitopes. A particularly preferred tag is described in the examples.

After the cells have been successfully transfected, they may be recovered for use as described. In the case of transfected cell lines, the cells may be expanded or subcultured onto fresh tissue culture media to produce large amounts thereof, or stored in liquid nitrogen for later use.

Production of Antisera

The stable transfected cells of the invention are used as an immunogen, eliciting production of antisera (alloantisera) to the heterologous MHC protein when the cells are administered to an immunologically competent animal. As mentioned hereinabove, to limit production of antibodies against proteins other than the desired epitopes of the heterologous MHC protein, the immunized animal should be substantially histocompatible with the original host cells, sharing the same BF allele and substantially the same histocompatibility antigens. Therefore, in the preferred embodiment, when using transfected immortal or tumor cell lines, the cells are administered to normal, healthy birds of the same inbred, congenic, or hybrid chicken lines from which the cell lines were derived. Alternatively, when using the transfected adult skin fibroblasts, the cells may be administered to the same bird from which the fibroblasts were first isolated.

The transfected cells may be administered to a target animal by a convenient route, such as by intravenous injection. To facilitate administration, the cells are generally formulated with a conventional physiologically acceptable carrier or diluent. Optionally, formulations may further include vaccine stabilizers or adjuvants known in the art. The formulations may be stored for short periods of time under refrigeration, or in frozen or lyophilized form.

The transfected cells are administered in an amount effective to elicit a protective immune response (antibody production) against the heterologous MHC protein, as compared to an untreated control. Suitable amounts may be readily determined by the practitioner skilled in the art, and will vary with the age and size of the bird and its overall vigor. Without being limited thereto, preferred dosages are greater than or equal to about $1\times10^6$ cells, particularly about $1\times10^7$ cells, per injection. The antigens should be administered in a plurality of doses, at least about five times (hyperimmunized). In the particularly preferred embodiment, best results have been achieved when $1\times10^7$ cells were administered approximately twice a week for about two and one half weeks, followed by approximately once a week for another one to three weeks or until completion of antisera collection.

Alloantisera (sera or plasma) containing antibodies against the heterologous MHC protein may be collected directly from the immunized birds using techniques conventional in the art. Briefly, blood may be collected at regular intervals, and sera separated by clotting and decantation and or by centrifugation, or plasma obtained free from heparinized blood. Sera or plasma free of erythrocytes may be used directly or frozen and stored at about −20° C. In accordance with this invention, either sera and plasma may be produced and used as described. All references to the collection of antisera or sera herein are equally applicable to plasma.

The antisera produced in accordance with this invention exhibit substantially reduced cross reactions with class I and/or class IV MHC proteins from birds of different haplotypes. The antisera may be used to determine the BF haplotype (BFIV allele) of unknown birds using a variety of conventional immunosorbent assays. The particular assay format used may be selected by the practitioner skilled in the art and is not critical. In accordance with the preferred embodiment, conventional hemagglutination assays are used. Briefly, a suspension of red blood cells from the unknown sample is incubated with the antisera and examined for agglutination as an indication of antibody binding. The antisera produced can also be used in a conventional indirect immunofluorescence assay as described by Fulton et al. (1996, ibid). This allows the examination of reactivity with antigens on lymphocytes. It is envisioned that in some instances the antisera may be used alone. However, because the class I MHC proteins are highly conserved among different haplotypes, and different haplotypes may share common epitopes, it is preferred to conduct the assay with a panel of antisera generated against class I MHC proteins of birds of different haplotypes. These other antisera may be conventional or prepared in accordance with the techniques of this invention.

The following examples are intended only to further illustrate the invention and are not intended to limit the scope of the invention which is defined by the claims.

EXAMPLE 1

To investigate the physical structure of the chicken class I glycoprotein, the cDNA representing the BFIV locus from the B21 haplotype were cloned and sequenced. To ensure detection of the cloned sequences a unique epitope tag was attached to the cDNA. With this tag, expression of the BFIV glycoprotein could be monitored even if allo-antiserum binding epitopes were altered. Normal and mutant class I glycoproteins were expressed in a chicken B-cell line (RP9) using an avian retroviral vector and then used to identify functionally important residues in the chicken class I ARS by both antibody binding studies and $^{51}$Cr release assay to measure cytotoxic T lymphocytes. Residues BF78 and 81 (HLA79 and 82) form an antibody epitope consistent with their predicted orientation based on HLA-A2 crystal structure. Changes in residue 34 dramatically alters antigen presentation by BFIV, but does not influence antibody binding due to the predicted orientation of the amino acid residues toward the inside of the molecule.

Materials and Methods

Chicken Lines

Chickens lines used included the inbred RPRL 15.B congenic lines (Shen et al., 1984, Poultry Sci., 63–1083) or the non-inbred line 0 (Astrin et al., 1979, Nature, 282:339, and Crittenden et al., 1984, Avian Dis., 28:1037) developed at the USDA Avian Disease and Oncology Lab in East Lansing, Mich. The congenic lines are 99.9% identical to the inbred $15I_5$ line, but differ at the MHC. The MHC haplotypes used in this study were B2, B5, B15, and B21 and represent common haplotypes found in commercial white Leghorn strains. The B21 sequence was cloned from the 15.N-21 congenic line. The original source of the B21 haplotype was line N from Cornell (Cole, 1968, Avian Dis., 12:9). Line 0 birds (B21/B21 haplotype) were used as the source of effector cells for cytotoxic T lymphocyte assays. Chick embryo fibroblasts (CEF) were obtained from 10-day-old embryos from line 0 chickens. LSCC-RP9 (RP9) is a B-cell lymphoblastoid cell line induced in a $15I_5\times7_2$ chicken (B2/B15 haplotype) by Rous associated virus-2 (RAV-2), a subgroup B avian leukosis virus (ALV) (Okazaki et al., 1980, Avian Pathol., 9:311). In addition, $15I_5\times7_2$ chickens were also used as recipients of transfected RP9 cells for the production of antisera.

Enzymatic Amplification

The polymerase chain reaction (PCR) conditions used were 200 mM of each dNTP, 2.0 mM $MgCl_2$, 10 mM Tris-HCl pH 8.3, 50 mM KCl 2.5 U AMPLITAQ (Perkin-Elmer), with 100 pM of each primer and 100 ng of template in a 100 ul final volume. Reaction mixtures were overlaid with light mineral oil (Sigma, St. Louis, Mo.) and placed in an MJ (Watertown, Mass.) thermocycler for an initial 1 min 96° C. denaturation step. This was followed by 30 cycles of amplification (denaturation 1 min 95° C., annealing 1 min 50° C., extension 3 min 72° C.) and a final extension of 10 min 72° C. The subsequent products were then ethanol precipitated before further manipulation.

Cloning and Sequencing

The cloning and sequencing strategies used are described in detail elsewhere (Hunt et al., 1994, ibid). Bursal mRNA was obtained from 15.N-21 B-homozygous chickens and cDNA was produced. Primers specific for the untranslated flanking regions of B-FIV locus were developed using the B12 genomic sequence (Kroemer et al., 1990, ibid). These primers, BFIV.5 and BFIV.3 (SEQ ID nos. 14 and 15, respectively) (see table 1) incorporated HindIII and XbaI restriction sites (underlined) and were used with PCR amplification to amplify the BFIV allele from B21 cDNA. The 1274 bp band obtained was cloned into the pRC-CMV eukaryotic expression vector (Invitrogen, San Diego, Calif.) using the HindIII and XbaI sites. Single-stranded sequence analysis was done in both directions for 2 separate clones using Taquence with 7-deaza nucleotides (USB, Cleveland Ohio).

Retroviral Vector Construction

An avian retroviral vector (RCASBP(A)); (Hughes et al., 1987, J. Virol., 61:3004) was used to express the BFIV cDNA in the RP9 B-cell tumor line. The presence of an endogenous poly A signal in sequences cloned into RCAS can interfere with retroviral expression of the inserted sequence. To eliminate this problem, the alpha 3 domain of BFIV21 was PCR amplified using primers specific to exon 3 (primer 15.5; SEQ ID no. 16; nt 511, table 1 and FIG. 2) and a region 95 bp upstream of the poly A site but still within the non-coding region of exon 8 (primer 14.3; SEQ ID no. 17; nt 1135; incorporating an XbaI site at nt 1155). The subsequent product lacked the endogenous poly A signal and was substituted into the Bpu1102I (nt 615) and XbaI (nt 1155) sites of BFIV21. This modified BFIV21 sequence was used for all subsequent manipulations.

Figure 3:
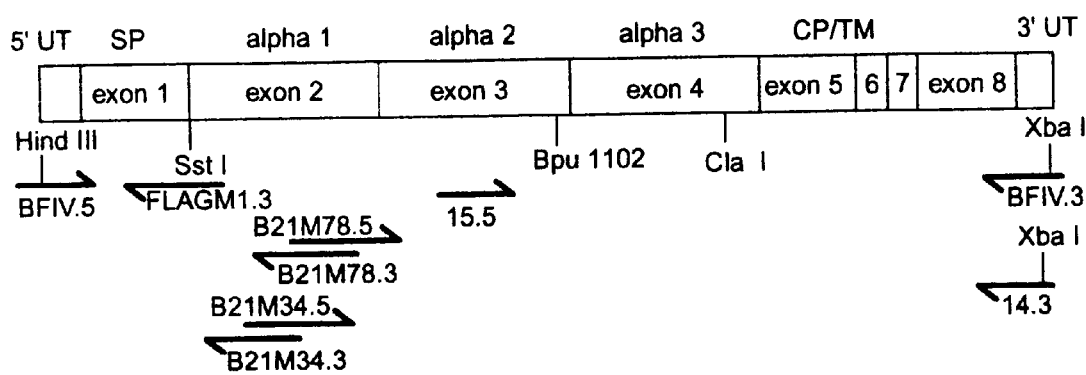

The BFIV21 sequence was transferred into the pUC Cla112N adaptor plasmid using the HindIII and XbaI restriction sites within the poly-linker (Hughes et al., 1987, ibid). It was then cloned into the ClaI site of RCASBP(A) using partial digestion (due to the internal ClaI site in BFIV21). Orientation of the insert with respect to the retroviral LTR was determined by PCR screening using a primer specific for the LTR of ALV and a BFIV21 internal primer. FIG. 3 shows the orientation and relative location of all primers used for amplification and those restriction endonuclease sites utilized for cloning.

The DH5 alpha *E. coli* strain was used for all transformations. Plasmid DNA was purified by either $CsCl_2$ centrifugation or Qiagen plasmid purification columns (Qiagen, Chatsworth, Calif.).

Production of Mutants

The FLAG epitope is a hydrophilic, 8 amino acid peptide available from Kodak-IBI (New Haven, Conn.). The FLAG coding sequence was introduced into BFIV21 by PCR amplification using primer BFIV.5, which is specific to the 5' end of BFIV, and primer FLAGM1.3 (SEQ ID no. 18), which is specific to the junction of exons 1 and 2 and also contains the 24 nucleotide sequence coding for FLAG (see table 1 and FIG. 3). This amplified product (consisting of exon 1, FLAG and 5' end of exon 2) was substituted between the HindIII and SstI sites of pUCBFIV21 and resulted in the pUCBFIV21FLAG construct. This was subsequently moved into the RCASBP(A) vector as previously described.

The BFIV21 mutants were produced using splicing by over-lapping extension (Ho et al., 1989, ibid). Mutagenizing primers 21M34.5 and 21M34.3 (SEQ ID nos. 19 and 20, respectively) (see table 1 and FIG. 3) were specific for the area to be altered (nt 193 and 195) and contained the desired mutant nucleotide sequence (indicated in bold in table 1). Each primer was used in PCR amplification in conjunction with a flanking primer (ie. BFIV.5 and 21M34.3 or 14.3 and 21M34.5) in separate reactions with BFIV21FLAG as template. The resulting product of each reaction was gel isolated from the template and combined for a second PCR amplification. Due to the nature of the mutagenizing primers, these products contain overlapping complementary ends which can anneal. The second PCR amplification utilized the same flanking primers (BFIV.5 and 14.3) with the annealed product as template. The product from this second PCR amplification was inserted into the HindIII and Bpu1102I sites of pUCBFIV21 and resulted in the pUCBFIV21M34TFLAG mutant. The amino acid sequence of B21M34T differs from that of B21 only at amino acid 34 in which the M of B21 is altered to T. The pUCBFIV21D78G,R81QFLAG mutant was generated in a similar manner utilizing the 21M78.3 and 21M78.5 set of mutagenizing primers (SEQ ID nos. 21 and 22, respectively). The B21D78G,R81Q mutant has amino acids G78 and Q81 instead of D78 and R81 found in B21. Each of the mutant constructs were shuttled into the pcDNA3 expression vector (Invitrogen, CA) to obtain single-stranded DNA for sequencing, and into the RCASBP(A) retroviral vector for subsequent expression analysis.

Cell Transfections and Infections

All cells were grown in LM media (64% Leibowitz L15, 36% McCoy SA) supplemented with 10% fetal calf serum, 2% tryptose phosphate broth and $1 \times 10^5$ U pen/strep per liter. Transfections into secondary CEF were done using $CaCl_2$/DNA co-precipitation. CEF were screened for BF transgene expression within 7 days of initial transfection by either alloantisera or FLAG-specific monoclonal antibody staining and subsequent flow cytometric analysis. RP9 cells were subsequently infected with the various constructs by overnight incubation with supernatant from CEF carrying the RCASBFIV21 constructs. Ten days after infection, the RP9 cells were stained with FLAG-specific monoclonal antibody (M2) and positive stained cells were sorted by flow cytometry (FACSort, Becton-Dickinson). This resulted in the various cell lines used in the antibody binding and cytotoxic T lymphocyte assays described.

Fluorescent Labeling and Detection

Peripheral blood lymphocytes (PBL) for screening antisera were obtained from the 15.B congenic lines and were purified with a Histopaque 1077 (Sigma, St. Louis, Mo.) gradient. Anti-B21 antiserum 7283 was produced by a B2/B15 bird and 7286 was produced by a B5/B15 bird following multiple immunizations with B21/B21 bursal cells.

Cells were incubated on ice with either B21-specific alloantisera (7283 or 7286) or FLAG-specific monoclonal antibody (M2) for 30 min. Cells were washed twice and then incubated for another 30 min with either FITC-labeled anti-chicken IgG (Bethyl Laboratories, Montgomery Tex.) or FITC-labeled anti-mouse IgG, M or A (Cappel, West Chester, Pa.). Cells were washed three times before flow cytometry analysis.

Cytotoxic T Lymphocyte Assay

Cytotoxic T lymphocyte (CTL) assays were performed as described by Thacker (1995, J. Virology, 69:6439–6444). Briefly line 0 birds were immunized iv with 2×10$^4$ infectious units of RAV-1-SRA (a recombinant subgroup A avian leukosis virus, originally supplied by Dr. H. Robinson) (Brown et al., 1992, Avian Dis., 36:515). Ten days after immunization, PBL from 2–5 birds were isolated on a Histopaque-1077 gradient (Sigma, St. Louis Mo.) pooled and washed, and then used as effector cells. Target cells were RP9 cells expressing either B21, B13, B21D78G,R81Q or B21M34T class I sequences as described above in addition to the endogenous B2 and B15 haplotypes. These target cells also express ALV viral products due to the RCAS transfection. Effector cells were incubated with $^{51}$Cr labeled target cells for 4 hr at E:T ratio of 100:1, 50:1, 25:1 and 12:1. Cytotoxicity, as measured by 51Cr release from the target cells was calculated as a proportion of the maximum released following N-P40 lysis of labeled target cells.

$$\% \text{ lysis} = \frac{(E - S)}{(M - S)} \times 100$$

where $E = CPM$ experiment
$S = CPM$ spontaneous
$M = CPM$ maximum $^{51}$Chromium release was determined from duplicate samples with a gamma counter (Micromedic). Spontaneous release was determined from cells incubated with media only, and maximum release was obtained from cells lysed with 1% detergent.

Results

Nucleotide Sequence of BFIV21

The nucleotide sequence of the cloned 1274 bp BFIV21 cDNA is given in FIG. 2. The sequence contains a portion of the 5' untranslated (UT) region, exon 1 which codes for the signal peptide, exons 2, 3 and 4 which code for the alpha 1, 2 and 3 domains, exons 5, 6, 7 and 8 which code for the transmembrane and cytoplasmic domains, and a portion of the 3' UT region including the polyadenylation tail. Both of the BFIV21 cDNA clones sequenced have the alternate exon 7.

The predicted amino acid sequence of BFIV21 was aligned with the BFIV12 (Guillemot et al., 1988, ibid) and BFIV19v1 (Kaufman et al., 1992, ibid) sequences (FIG. 4). The polymorphic amino acids occur primarily in the alpha 1 and alpha 2 domains (20.5% and 15.4% polymorphic respectively) with the alpha 3, transmembrane and cytoplasmic domains being relatively monomorphic (<2% polymorphism overall). The human HLA-A2 amino acid sequence is shown aligned with BFIV, with gaps inserted in either BF or HLA-A2 for maximal alignment. The glycosylation site (CHO) found in both chicken and mammalian class I glycoproteins is identified. An additional glycosylation site at BF N39 was found for all three BFIV alleles. This glycosylation site lies within a very conserved stretch of amino acids, and is probably a conserved feature of the BF glycoprotein.

The nucleotide sequence for the FLAG epitope was engineered onto the amino terminal end of the BFIV21 cDNA sequence and expressed in conjunction with the BFIV sequence by using the RCAS retroviral vector. Expression of this epitope, as detected by a FLAG-specific monoclonal antibody (M2) is shown on different cell lines (table 2). The FLAG epitope was detected only on the cell line containing the construct with the FLAG epitope (RP9-BFIV21FLAG) confirming the monoclonal antibody specificity. Expression of the BFIV21 glycoprotein was detected by two B21-specific alloantisera 7283 and 7286 (produced by B2/B15 and B5/B15 chickens respectively). Each of them recognize the B21 haplotype, but 7283 also cross-reacts with PBL of the B5 haplotype (see table 3). Neither antisera cross-reacts with PBL of the B2 or B15 haplotype (present on RP9 cells) or against any other haplotype tested (data not shown). The presence of the FLAG epitope did not interfere with recognition of BFIV21 epitopes by either of these alloantisera.

Expression of FLAG epitope and BFIV21

Table 3 summarizes evidence for the expression of FLAG and B21 epitopes on the cell lines transfected by either RCASBFIV21FLAG or one of the RCASBFIV21FLAG-mutants. For simplicity, the cell lines from here on will be referred to as B21, B21M34T or B21D78G,R81Q even though they all also express the FLAG epitope. The FLAG epitope is expressed at a similar level on all three cell lines but is absent on the RP9 cell line as indicated by binding of the FLAG-specific monoclonal antibody (M2). The B21-specific alloantisera (7283) recognized all three B21-expressing cell lines. However, it reacted to the B21 and B21M34T cell lines at a higher level than the B21D78G, R81Q cell lines. This difference in detection was consistent in five assays and was probably due to the lack of a B21 specific epitope recognized by 7283. Absorption of 7283 antiserum with B21M34T expressing cell line removed all B21 specificity. In contrast, absorption with the B21D78G, R81Q expressing cell line removed all specificity to B21D78G,R81Q but left considerable reactivity for both the B21 and B21M34T cell lines. The crystal structure model predicts that the side chains of those amino acids altered in B21D78G,R81Q (BF78 and 81; HLA 79 and 83) should point away from the ARS and be available for antibody interaction. Since B21D78G,R81Q lacks only this epitope, absorption with B21D78G,R81Q should remove all B21 specificity except antibodies specific to this region. Absorption with RP9 did not alter B21-specificity of 7283 antiserum. The 7286 antiserum also recognized all three B21 expressing cell lines, but at a lower level than 7283. Absorption of this antiserum with any of the B21 expressing cell lines (either normal B21 or mutant) removed all B21 reactivity.

The lower portion of table 3 shows that alloantiserum 7283 binds to PBL from the B5 haplotype in addition to B21. Absorption with the B21M34T cell line removed all B21 specificity for PBL (as was seen with the mutant cell lines) and also removed the B5 cross-reacting antibodies. Absorption with the B21D78G,R81Q cell line removed some of the B21 activity; however some activity remained for B21 and B5. The alloantiserum 7286, produced by a B5/B15 individual, was not expected to have any B5 specificity. Thus it reacted with PBL having the B21 but not B5 haplotype. Absorption with either of the B21 mutant cell lines removed all specificity for B21 PBL as expected.

Cr-release Assay

Figure 5:
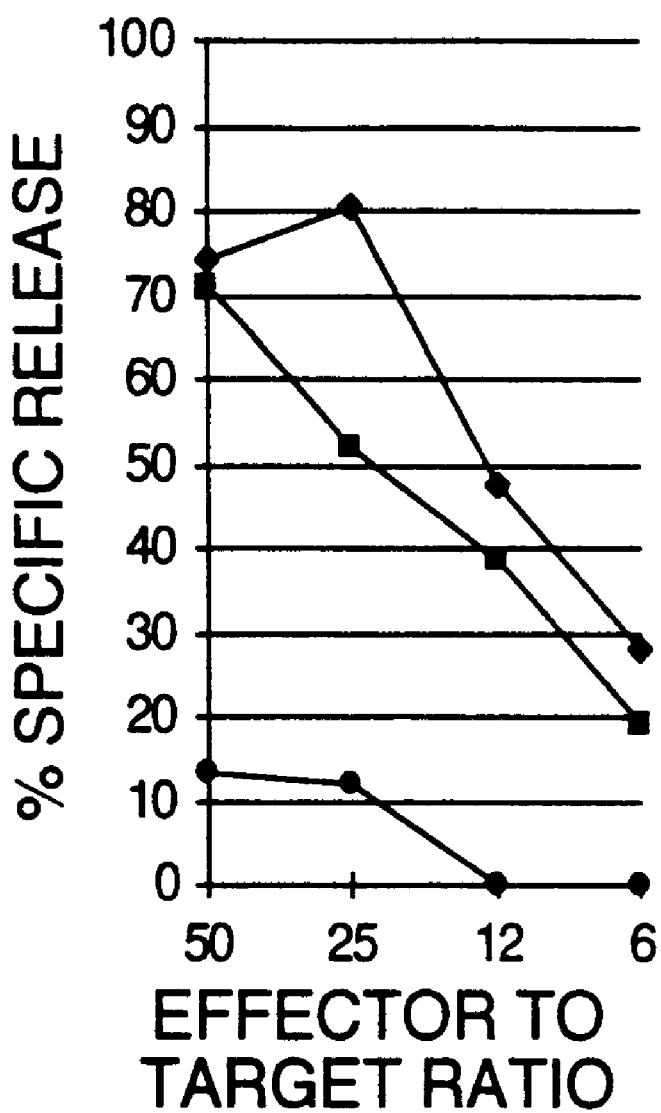

A CTL assay was done using RP9 target cells expressing either BFIV21 or BFIV21FLAG to determine if the FLAG epitope interfered with the ability of BFIV to interact with T cell receptor. RP9 cells expressing a non-MHC matched class I (BFIV13FLAG) were used as a negative control (FIG. 5). The CTL assay was repeated several times with the same results, i.e. FLAG did not affect lysis by CTL.

Figure 6:
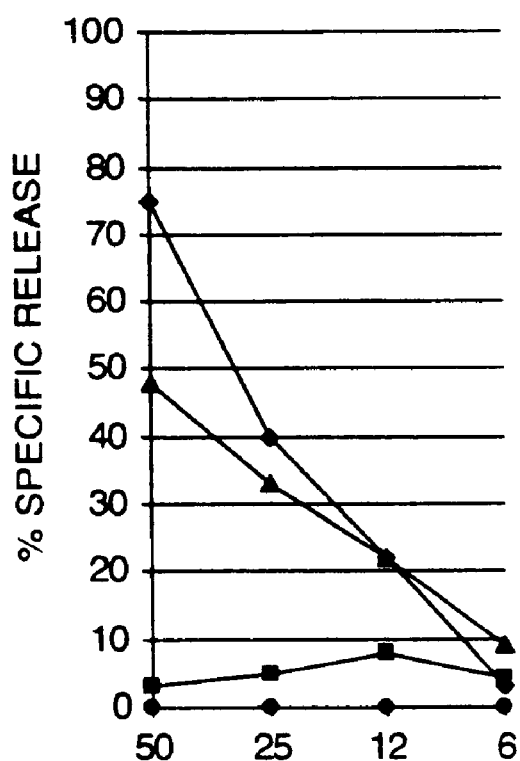
Figure 6:
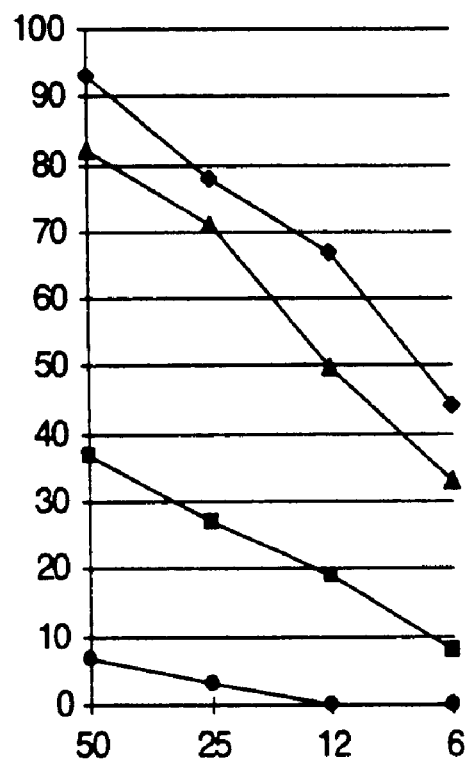

FIG. 6 shows the results of two independent CTL assays using the RP9 target cell lines expressing either of the BFIV21, BFIV13, B21M34T or B21D78G,R81Q class I glycoproteins. Effector cells were PBL obtained from ALV infected birds of B21/B21 haplotype. At each effector:target ratio there was lysis of the BFIV21 and B21D78G,R81Q expressing target cells as indicated by the percent specific release of $^{51}Cr$; however, lysis of B21D78G,R81Q target cells was consistently lower. The BFIV13 target cells represent an MHC-incompatible negative control and had either very low or no lysis. The target cells expressing the B21M34T mutant showed almost no lysis in one assay and a low level of lysis in the second assay. While these results show variation between assays, the trends are consistent: lysis of B21D78G,R81Q cells is slightly less than the positive control BFIV21, and lysis of B21M34T is considerably less than BFIV21 but greater than the negative control of BFIV13.

Discussion

Based on the alignment of BFIV and HLA-A2, amino acids BF 78 and 81 are predicted to be equivalent to HLA 79 and 82 and thus should be on the alpha helix with their side chains directed away from the antigen binding groove and exposed for antibody interaction. This is the same region as the Bw4/Bw6 serologic epitope of HLA-A32 (Wan, et al., 1986, J. Immunol., 137:3671) and an alloreactive site in both HLA-B7 (Walker et al., 1985, ibid) and mouse H-2Kb (Hammerling, 1982, P.N.A.S. USA, 79:4737). B21-specific alloantisera should contain antibodies specific to this region in addition to other epitopes of the BF21 glycoprotein. This region is not predicted to be very important in peptide presentation since it is on the alpha helix and the side chains are directed away from the ARS; however, it may have some influence on T cell receptor interaction. The BFIV residues 78 and 81 are D (hydrophilic and acidic) and R (hydrophilic and basic) in BFIV21 versus G and Q (both are hydrophilic but neutral) in the BFIV12 and BFIV19v1, alleles, as well as in the B21D78G,R81Q mutant. Thus, the mutations made in B21D78G,R81Q result in a major alteration of side-chain chemistry in this region. The G78 and Q81 residues are also found in the BFIV15 (Hunt et al., 1994, ibid) and BFIV2 alleles. The results of the alloantibody binding and absorption experiment using this mutant were very informative. Expression levels of the various constructs in the cell lines were similar as shown by the level of binding of the FLAG-specific M2 antibody. There was variation in binding of the two B21-specific alloantisera to the different cell lines suggesting alteration of alloantisera binding sites. The lowered binding of 7283 to the B21D78G,R81Q cell line suggested that the mutant lacked an epitope recognized by the antisera. The B21D78G,R81Q mutation was designed to lack the BF D78-R81 epitope of B21. Absorption of 7283 with B21D78G,R81Q removed all activity to B21D78G, R81Q but left reactivity to B21. Antibodies also remained to B21 and B5 PBL. The antibodies to BF21 epitopes had all been removed except for those specific to the D78-R81 region. Interestingly, this same D78-R81 polymorphism seen in BFIV21 also occurs in the BFIV5 sequence and may explain the B5 cross-reactivity commonly seen with B21-specific antisera. The significance of the D78-R81 epitope in haplotype specificity was confirmed with the absorption experiment utilizing the second B21-specific alloantiserum, 7286. This antiserum was produced in a B5/B15 individual and was thus not expected to contain antibodies against this region. The absorption data confirmed the lack of D78-R81 epitope antibodies in 7286.

The second region to be altered (BF residue 34) was selected because, according to the HLA-A2 crystal structure, this amino acid should be on a beta strand directly underneath the alpha helix and thus not exposed for antibody interaction. This residue should be significant in peptide presentation as it is predicted to contact the main chain carbon of the peptides bound in the antigen recognition site (Saper et al., J. Mol. Biol., 1991, 219:277). In the BFIV21 allele, BF34 is M (large, sulphur-containing, neutral) versus T (smaller, neutral) in BFIV15, BFIV19v1 and the BFIV21M34T mutant. The BFIV12 and BFIV19 haplotypes both have a V at position 34 (Hunt et al., 1994, ibid). Absorption of 7283 with the B21M34T cell line removed all B21-specificity confirming the prediction that B21M34T was serologically identical to B21. The results of the CTL assay clearly show the significance of residue 34 in peptide binding. The change of M to T in the B21M34T mutant greatly decreased the ability of this cell line to be a target for CTL.

EXAMPLE 2

Materials and Methods

Chickens and Aloantisera

Birds used were from the 15I$_5$B congenic lines developed at the USDA Avian Disease and Oncology Lab in East Lansing (Shen et al., 1982, ibid). The congenic lines are 99.9% identical to the inbred 15I$_5$ line, but differ at the MHC B-haplotype. The original sources of the B haplotypes are; $B^2$ from line RPRL-6$_1$, $B^{12}$ from Reaseheath line C and $B^{13}$ JM-P. Production and specificity of the MHC-specific alloantisera used were described by Fulton et al. (1995, ibid). MHC-heterozygous birds were repeatedly immunized with eythrocytes from birds homozygous for a different MHC haplotype. Serum was harvested from clotted blood. Alloantiserum is identified by the B homozygous specificity of the donor cells, the heterozygous B-genotype of the recipient, and the wing-band number of the recipients, e.g., B13 (2/15) 10171 designates a B13 antiserum produced by a B2/B15 heterozygous bird number 10171. Alloantiserum were absorbed by incubating equal volumes of a 1/100 dilution of antiserum with cells of the appropriate haplotype for 15 mins. Monoclonal antibodies M1 and M2 were obtained from Kodak-IBI (New Haven, Conn.).

Cell Culture and Transfections

Cell Culture conditions were as described in Example 1 and Fulton et al. (1995, ibid). Briefly, cells were grown in Leibovitz L15 and McCoy 5A supplemented with 10% fetal calf serum and 2% tryptose broth. Transfections were done using calcium phosphate/DNA co-precipitation into chick embryo fibroblasts (CEF). Supernatant from the transfected CEF was used to infect the RP9 cell line. The infected cell lines were labelled with the FLAG-specific monoclonal antibody (M2) (Kodak-IBI) and positive cells were sorted by flow cytometry (FACSort, Becton Dickinson, San Jose, Calif.).

Fluorescent Labelling and Detection

RP9 cell lines expressing the various FLAG-BFIV constructs were collected and washed in tissue culture media. Cells were incubated with either a 1/100 dilution of B-specific antiserum or a 1/150 dilution of FLAG-specific antibody (M2) for 30 min, washed twice and then incubated another 30 min with either FITC-labelled anti-chicken IgG (Bethyl Laboratories, Montgomery, Tex.) or FITC-labelled polyclonal anti-mouse IgG, M, and A (Cappel, Westchester, Pa.). Cells were washed three times before analysis on a Becton-Dickinson FACSort. Dead cells were gated out by inclusion of propidium iodide.

Cloning and Sequencing

The cloning and sequencing strategies used were the same as in Example 1 and in Hunt et al. (1994, ibid). In review, bursal mRNA was obtained from B homozygous congenic chickens and cDNA was produced. Primers specific for the untranslated flanking regions of B-FIV genomic sequences (Kroemer et al., 1990, ibid) were used to PCR amplify cDNA from homozygous B2, B12 and B13 bursa. The 1274 bp band amplification product obtained was cloned into the pRC-CMV eukaryotic expression vector (Invitrogen). Single-stranded sequence analysis was done in both directions for 2 separate clones using TAQUENCE (USB, Cleveland, Ohio). Epitope tagging and transferring of these constructs into the expression vector has been described in detail in Example 1 and Fulton et al. (1995, ibid). Briefly, the BFIV sequences from the B12 and B13 haplotypes were epitope-tagged with the FLAG sequence and then transferred into the RCASBP retroviral expression vector. All of the expression constructs contain exon 1 (signal peptide) and exon 4 (alpha 3 domain) of BFIV21, with the nucleotide sequence encoding the FLAG epitope at the 3' end of exon 1 (amino terminal of the alpha 1 domain). Between exons 1 and 4, we have inserted exons 2 and 3 (alpha 1 and 2 domains) of various inate (BFIV12, BFIV13) and mutant BFIV alleles.

BFIV21 exons 1 and 4 were used in the expression constructs of this example to simplify cloning and expression by using the same techniques described in Example 1 for the BFIV21 mutant. These exons contain relatively few polymorphisms and are generally conserved among the haplotypes. It is envisioned that expression constructs for other BFIV allels may be prepared in the same manner.

The DH5 alpha *Escherichia coli* strain was used for all transformations. Plasmid DNA was purified by either $CsCl_2$ density gradient or Quiagen plasmid purification columns (Quiagen, Chatsworth, Calif.).

In vitro Mutagenesis

Development of the BFIV-FLAG constructs was described in Example 1 and Fulton et al. (1995, ibid). As in Example 1, the BFIV13 mutants were produced using splicing by overlapping extension. Mutagenizing primers specific for the area to be altered and containing the desired mutant nucleotide sequence were designed for PCR amplification of cloned BFIV template from the appropriate haplotype. The oligoprimers designed for the production of the B13m126 and B13m150 mutants are shown in Table 4. The mutant nucleotides are superscripted and the non-mutant bases are subscripted. The B12m147 mutant was designed based on the identity in amino acid sequences of BFIV2 and BFIV12 between aa 25 to 146 and 156 to 334. The cDNA fragment encoding aa 81 to 175 was removed from the BFIV2 sequence using Pstl and Bpu1102 restriction endonuclease sites. This BFIV2 DNA fragment was inserted into the equivalent region of the BFIV12 sequence. Each of the mutant constructs were shuttled into the pcDNA3 vector to obtain single stranded DNA for confirmation of sequence. Table 5 summarizes the mutants and shows the location of the amino acids that were changed, and the normal and subsequent mutant acid sequence.

Results

BFIV Amino Acid Sequences

When the amino acid sequences of the BFIV locus from the 12, 2 and 13 haplotypes are aligned, in the alpha 1 domain, the amino acid sequences of BFIV2 and BFIV12 are identical except for three polymorphic amino acids within the first 24 amino acids. In the alpha 2 domain, B2 and B12 alleles are identical except for the region of aa 147–155 in which 7 out of 9 amino acids differ. Beyond this region, these two alleles are identical.

Comparison between BFIV12 and BFIV13 sequences shows only one polymorphism in the first portion of the alpha 1 domain whereas four polymorphic regions occur between amino acids 53 to 88. BFIV13 has numerous polymorphisms not found in either of the other alleles in the alpha 2 domain. At aa 147–155, BFIV13 shares all 7 of the 9 polymorphisms found in the BFIV12 allele. In this region, the BFIV2 allele in identical to published sequences from BFIV alleles from B15, B19, B19v1 (Hunt et al., 1994, ibid, and Kaufman et al., 1992, ibid) and B5 and B17 haplotypes. The BFIV21 allele has a G at aa 148 but is otherwise identical to BFIV2 in this region (Fulton et al., 1995, ibid). Beyond aa 155 and including the alpha 3 domain, all three of the alleles are almost identical except for two ploymorphisms near the end of the transmembrane domain of BFIV13.

The BFIV amino acid sequences were aligned with those of the HLA (see Fulton et al., 1995, ibid) and those amino acids that are polymorphic between BFIV12 and the BFIV2 and BFIV13 alleles were identified using the crystal structure of the HLA-A2 class I molecule. Those polymorphic residues predicted to interact with peptide in the antigen binding groove were indicated, as were those predicted to interact with the T cell receptor, and residues with no predicted antigen presenting function. Amino acid gaps were introduced as needed to align the two sequences. Examination of the model of the class I glycoprotein shows that the polymorphic amino acids in the alpha 1 domain distinguishing B2 from B12 occur primarily buried within the molecule, under the alpha helix. However, aa 147–155 of the alpha 2 domain are located on the helix, a position predicted to be involved in TCR interaction and/or antibody interaction. In contrast, B13 differs from B12 in numerous exposed areas, including the alpha helix of alpha 1 domain and a beta strand connecting loop.

The BFIV13 allele has two major clusters of amino acid polymorphisms. Residues 126–128 are on a loop potentially exposed for antibody interaction, but probably not involved in either Tcr binding or peptide interaction because of their external location. The change from consensus of GTM to DMK (unique to B13) results in major changes in physical properties of the region. The second major cluster (aa 147–155) is found on the second alpha helix of the alpha 2 domain and these polymorphisms are common with B12. With one exception (aa 150), all of these substituted amino acids are predicted to affect either Tcr binding or peptide interaction. The location of this region on the upper surface of the helix may also result in an antibody interacting epitope.

In order to determine the significance of the polymorphic regions identified in the BFIV sequence analysis, specific mutations were induced in the B12 and B13 sequences. The amino acid sequences altered in the parental allele and the subsequent mutants are summarized in Table 5. Each mutant is identified by the BFIV parental genotype and the amino acid modifications that were done. The B12m147 mutant sequence is identical to that of B12 except that aa 147–155 was altered to GDYAEGLKQ (SEQ ID NO. 32) found in B2. Within the B13 allele, the DMK cluster unique to B13 was altered to GTM, resulting in the B13m126 mutant. The B13m150 mutant has a single amino acid change at aa150 from P found in both B12 and B13 to A found in B2.

Expression of BFIV Sequences

BFIV expression of the various chimeric constructs was detected by monoclonal antibody and B-specific alloantisera. The FLAG-specific M1 antibody has been previously shown to bind to those cell lines expressing the transfected FLAG-BFIV construct (Example 1 and Fulton et al., 1995, ibid). Expression of each transfected FLAG-BFIV chimeric glycoprotein was confirmed for each cell line. The B13-specific alloantiserum 10171 (made in a 2/15 heterozygote) cross-reacts with peripheral white blood cells (WBC) of the B12 and B13 haplotypes but not B2 (Fulton et al., 1996, ibid). Unabsorbed 10171 binds to BFIV12 and BFIV13 expressing cell lines showing that the crossreactivity is due, at least in part, to BFIV epitopes. This antiserum adsorbs to both B13m126 and B13m150 expressing cell lines, but not the B12m147 cell line. Absorption of 10171 with B12 removed antibodies directed against B12 epitopes but antibodies recognizing B13 remained. Absorption with B12m147 did not affect binding of 10171 to the cell lines. Absorption with B13m126 left residual antibodies to B13 and B13m150. B13 absorption removed all antibodies with B13m150.

The second B13-specific antiserum 497H (12/19) was expected to contain a spectrum of antibodies different from that of 10171 because it was produced by a 12/19 individual. 497H did not contain antibodies that recognized B12 or B12m147, but did adsorb to the cells expressing the B13 or B13 mutant construct. Absorption with B13m126 left reactivity to B13 and B13m150. Absorption of this serum with either B13 or B13m150 expressing cells removed all antibodies.

The B12 antiserum 10197 (made in a 5/15) cross-reacted with WBC of both the B12 and B13 haploytypes (Fulton et al., 1995, ibid). Unabsorbed, this antiserum bound to both B12 and B13 expressing cell lines showing the presence of antibodies directed against BFIV epitopes common to these alleles. This antiserum also bound to both the B13 mutants, but had minimal reactivity to B12m147. Absorption with B12m147 did not affect binding of this antibody to the various cell lines; however, the background staining of B12m147 was decreased. Absorption with the B12 expressing cell line removed all antibodies.

The alloantiserum absorption by cells expressing different BFIV mutant glycoproteins was informative for identification of amino acids forming antigenic epitopes involved in cross-reactivities. The B13 specific alloantiserum 10171 reacted with the cell line that expressed BFIV12 as well as the cell line expressing BFIV13. This demonstrated that the cross-reactivity of this antiserum to WBC from B12 and B13 haplotypes is due to a common BFIV epitope as hypothesized by Fulton et al. (1996, ibid). The B12m147 mutant is identical to B12 except that the sequence of amino acids 147–155 was altered to that of B2. The lack of B13 antiserum adsorption to the B12m147 mutant cells shows that the altered region contains a major antigenic epitope responsible for the B12 and B13 cross-reactivity. The B13m150 mutant was antigenically comparable to B13. This suggested that the P to A change in the B13m150 mutant did not significantly alter an antibody binding site. The buried location of amino acid 150 in the protein may have minimized any antigenic change in this region. The B13m126 mutant showed that the amino acids 126–128 region contains an antigenic epitope since absorption of B13 specific antiserum with this mutant did not remove all of the B13 antibodies. This suggests that a significant antigenic epitope had been altered in the B13m126 mutant.

The demonstration that the region of amino acids 126–128 of BFIV13 contains a unique antigenic epitope enables the production of BFIV13 specific antiserum. For example, the DNA sequence encoding BFIV15 protein may be altered by site directed mutation as described above to change the epitope at amino acids 126–128 to the corresponding BFIV13 epitope. This may be accomplished by changing amino acids 127 and 128 of the BFIV15 protein to M and K, respectively (i.e., yielding a B15m127 mutant). Thus, amino acids 126–128 of the B15m127 mutant will then be DMK, the same as found on the BFIV13 molecule. Transfection of RP9 cells and subsequent immunization with the transfected cells as described above will produce antiserum specific for B13 (at the amino acids 126–128 epitope).

It is understood that the foregoing detailed description is given merely by way of illustration and that modifications and variations may be made therein without departing from the spirit and scope of the invention.

TABLE 1

Sequence of oligonucleotide primers used for cloning BFIV21 and for site-directed mutagenesis. Restriction endonuclease sites involved for cloning are underlined. Nucleotide alterations including the inserted FLAG sequence are indicated by bold text.

| Primer | Nucleotide Sequence | SEQ ID NO |
| --- | --- | --- |
| BFIV.5 | 5'GCGGGTACC | SEQ ID NO 14 |
| BFIV.3 | 5'GCGTCTAGAGCGGCCGCTGGCCCATCATTTTATTTCAC | SEQ ID NO 15 |
| 15.1 | 5'CACCAAGAGGAAATGGGAGG | SEQ ID NO 16 |
| 14.3 | 5'TGCTGGTCTAGACTGTTGGCTCCTTGCAGGC | SEQ ID NO 17 |
| FLAGM1.3 | 5'CAGGGTATGGAGCTCCTTGTCGTCGTCGTCCTTGTAGTCGGCCGCCGCCCCGCACAC | SEQ ID NO 18 |
| B21M34.5 | 5'CTCTTTTACGCACTACAA | SEQ ID NO 19 |
| B21M34.3 | 5'CTGTTGTAGTGCGTAAAGAG | SEQ ID NO 20 |
| B21M78.5 | 5'AACCTGGGAATACTGCAACGGCGCTAC | SEQ ID NO 22 |
| B21M78.3 | 5'GCGCCGTTGCAGTATTCCCAGGTT | SEQ ID NO 21 |

TABLE 2

Log fluorescent mean channel numbers showing expression on three cell lines of the FLAG epitope as detected by FLAG-specific monoclonal antibody M2 and BFTV21 as detected by B21-specific alloantisera 7283 and 7286

|  | anti-FLAG | Antibody B21-specific alloantisera | |
|---|---|---|---|
| Cell line[a] | mAb M2 | 7283 | 7286 |
| RP9-BFIV21 | 21[b] | 328 | 111 |
| RP9-BFIV21FLAG | 191 | 370 | 160 |
| RP9 | 20 | 63 | 60 |

[a] Cell types are RP9 expressing either BFIV21 or BFIV21FLAG, or non-transfected.
[b] Mean log fluorescent channel number.

TABLE 3

Log fluorescent mean channel numbers showing reactivity of unadsorbed and adsorbed alloantisera 7283 and 7286 on normal and mutant allele-expressing BFIV21 cell lines. Antisera were adsorbed with cell lines expressing either the BFIV21M34T or BFIV21D78G.R81Q mutant construct or the RP9 progenitor cell line

|  | anti-FLAG | anti-B21-7283 alloantiserum (2/15) adsorbed with: | | | | anti-B21-7286 alloantiserum (5/15) adsorbed with: | | | |
|---|---|---|---|---|---|---|---|---|---|
| Cell type[a] | mAb M2 | None | 21M34T | 21D78G | RP9 | None | 21M34T | 21D78G | |
| RP9-BFIV21FLAG | 565[b] | 557 | 35 | 191 | 524 | 233 | 25 | 28 | |
| RP9-BFIV21M34TFLAG | 546 | 633 | 47 | 237 | 599 | 284 | 46 | 50 | |
| RP9-BFIV21D78G.R81QFLAG | 525 | 412 | 45 | 37 | 325 | 260 | 44 | 41 | |
| RP9 | 16 | 45 | 37 | 30 | 33 | 36 | 29 | 29 | |
| PBL-B21 | 20 | 526 | 85 | 263 | 424 | 279 | 55 | 66 | |
| PBL-B5 | 20 | 533 | 98 | 299 | 613 | 67 | 68 | 64 | |
| PBL-B15 | 19 | 52 | 58 | 63 | 57 | 58 | 65 | 60 | |

[a] Cell types are either RP9 expressing the various BFIV21FLAG constructs or non-transfected, or peripheral blood lymphocytes (PBL) of the specified haplotype.
[b] Mean log fluorescence channel number.

TABLE 4

Sequence of oligonucleotide primers used for generating the site-specific mutants. Mutant nucleotides are superscripted and non-mutant nucleotides are subscripted.

| Primer | Nucleotide Sequence | | |
|---|---|---|---|
| B13M126.5 | 5' GAC AAA G$^G_A$C A$^C_T$G A$^T_A$G ACG TTC | SEQ ID NO 23 | SEQ ID NO 24 |
| B13M126.3 | 5' GAA CGT C$^A_T$T C$^G_A$T G$^C_T$C TTT GTC | SEQ ID NO 25 | SEQ ID NO 26 |
| B13M150.0 | 5' GAG AGT GAA $^G_C$CT GAG AGG TGG | SEQ ID NO 27 | SEQ ID NO 28 |
| B13M150.3 | 5' CCA CCT CTC AG$^C_G$ TTC ACT CTC | SEQ ID NO 29 | SEQ ID NO 30 |

TABLE 5

Location of the altered amino acids, the normal and subsequent mutant sequences of the three altered BFIV glycoproteins.

| Mutant | Location of Change | Normal | Mutant |
|---|---|---|---|
| BFIV12m147 | aa 147–155 | ESEPERWKN SEQ ID NO 31 | GDYAEGLKQ SEQ ID NO 32 |
| BFIV13m126 | aa 126–128

We claim:

1. A process of producing antisera against BFIV protein comprising:
  (a) administering a transfected cell line which comprises a host chicken tumor cell containing a recombinant DNA comprising a DNA sequence encoding a heterologous, recombinant BFIV protein inserted therein, and wherein said chicken tumor cell line is derived from a chicken selected from the group consisting of progeny of an inbred chicken line, and a hybrid of two different inbred chicken lines, and further wherein said transfected cell is effective for expression of said heterologous, recombinant BFIV protein, to a chicken in an amount effective to elicit an immune response against said heterologous, recombinant BFIV protein, wherein said chicken is selected from the same said group from which said cell line is derived, and
  (b) collecting antiserum or plasma containing antibodies to said heterologous, recombinant BFIV protein, wherein said heterologous, recombinant BFIV protein comprises an alteration in at least one epitope of wild-type BFIV protein, said heterologous, recombinant BFIV protein being effective for eliciting production of antibodies in said chicken having different binding specificity than antibodies produced against said wild-type BFIV protein.

2. A process of producing antisera against BFIV protein of the chicken Major Histocompatibility Complex comprising:

(a) administering a transfected fibroblast which comprises a host chicken cell containing a recombinant DNA comprising a DNA sequence encoding a heterologous, recombinant BFIV protein inserted therein, and wherein said host cell is an adult chicken skin fibroblast recovered from a chicken selected from the group consisting of a normal adult chicken, progeny of an inbred chicken line, and a hybrid of two different inbred chicken lines, and further wherein said transfected cell is effective for expression of said heterologous, recombinant BFIV protein, to a chicken in an amount effective to elicit an immune response against said heterologous, recombinant BFIV protein, wherein said chicken is selected from the group consisting of said normal chicken, progeny of said inbred chicken line or a hybrid of said two different inbred chicken lines, from which said fibroblast is recovered, and (b) collecting antiserum or plasma containing antibodies to said heterologous, recombinant BFIV protein, wherein said heterologous, recombinant BFIV protein comprises an alteration in at least one epitope of wild-type BFIV protein, said heterologous, recombinant BFIV protein being effective for eliciting production of antibodies in said chicken having different binding specificity than antibodies produced against said wild-type BFIV protein.

3. The process of claim 1 wherein said wild-type BFIV protein has the amino acid sequence of a haplotype selected from the group consisting B2, B5, B12, B13, B15, B17, B18, B19, B19v1, and B21.

4. The process of claim 2 wherein said wild-type BFIV protein has the amino acid sequence of a haplotype selected from the group consisting B2, B5, B12, B13, B15, B17, B18, B19, B19v1, and B21.

5. Antiserum or plasma produced by the process of claim 1.

6. Antiserum or plasma produced by the process of claim 2.

7. The process of claim 1 wherein said heterologous, recombinant BFIV protein is selected from the group consisting of (1) BFIV protein having an amino acid alteration at a site within an epitope of wild-type BFIV protein, and (2) BFIV protein comprising at least one heterologous epitope inserted within wild-type BFIV protein.

8. The process of claim 7 wherein said heterologous, recombinant BFIV protein comprises said BFIV protein comprising at least one heterologous epitope of a different BFIV allele inserted within said wild-type BFIV protein.

9. The process of claim 7 wherein said heterologous, recombinant BFIV protein comprises said BFIV protein having an amino acid alteration at a site within an epitope of said wild-type BFIV.

10. The process of claim 2 wherein said heterologous, recombinant BFIV protein is selected from the group consisting of (1) BFIV protein having an amino acid alteration at a site within an epitope of wild-type BFIV protein, and (2) BFIV protein comprising at least one heterologous epitope inserted within wild-type BFIV protein.

11. The process of claim 10 wherein said heterologous, recombinant BFIV protein comprises said BFIV protein comprising at least one heterologous epitope of a different BFIV allele inserted within said wild-type BFIV protein.

12. The process of claim 10 wherein said heterologous, recombinant BFIV protein comprises said BFIV protein having an amino acid alteration at a site within an epitope of said wild-type BFIV.

* * * * *